United States Patent
Tanaka

(10) Patent No.: US 11,430,581 B2
(45) Date of Patent: Aug. 30, 2022

(54) CONTACTLESS INFERNAL MEASUREMENT DEVICE, CONTACTLESS INTERNAL MEASUREMENT METHOD, AND INTERNAL MEASUREMENT RESULT DISPLAY SYSTEM

(71) Applicant: MAXELL, LTD., Kyoto (JP)

(72) Inventor: Yukinobu Tanaka, Tokyo (JP)

(73) Assignee: MAXELL, LTD., Kyoto (JP)

( * ) Notice: Subject to any disclaimer, the term of this patent is extended or adjusted under 35 U.S.C. 154(b) by 131 days.

(21) Appl. No.: 16/753,299

(22) PCT Filed: Oct. 4, 2018

(86) PCT No.: PCT/JP2018/037281
§ 371 (c)(1),
(2) Date: Apr. 2, 2020

(87) PCT Pub. No.: WO2019/070042
PCT Pub. Date: Apr. 11, 2019

(65) Prior Publication Data
US 2020/0243211 A1    Jul. 30, 2020

(30) Foreign Application Priority Data
Oct. 5, 2017 (JP) .............................. JP2017-195240

(51) Int. Cl.
*G21K 5/10* (2006.01)
*G01N 21/21* (2006.01)
*G01N 21/49* (2006.01)

(52) U.S. Cl.
CPC ............... *G21K 5/10* (2013.01); *G01N 21/21* (2013.01); *G01N 21/49* (2013.01)

(58) Field of Classification Search
CPC ........... G21K 5/10; G01N 21/21; G01N 21/49
(Continued)

(56) References Cited

U.S. PATENT DOCUMENTS 8,564,777 B1 * 10/2013 Herzinger ............ G01N 21/211
356/369
2007/0070357 A1    3/2007 Aiyer
(Continued)

FOREIGN PATENT DOCUMENTS

JP    S63-019016 A    1/1988
JP    S63-128211 A    5/1988
(Continued)

OTHER PUBLICATIONS

International Search Report issued in corresponding International Patent Application No. PCT/JP2018/037281, dated Jan. 8, 2019, with English translation.

*Primary Examiner* — Nicole M Ippolito
(74) *Attorney, Agent, or Firm* — McDermott Will & Emery LLP

(57) ABSTRACT

Provided is a contactless internal measurement device including an electromagnetic wave irradiation unit that irradiates an electromagnetic wave to a measurement subject, and an electromagnetic wave receiver that detects the electromagnetic wave reflected by the measurement subject. The electromagnetic wave irradiation unit is disposed to reduce a polarization component of the electromagnetic wave detected by the electromagnetic wave receiver, the polarization component being the same as a polarization component of the electromagnetic wave irradiated by the electromagnetic wave irradiation unit.

16 Claims, 29 Drawing Sheets

(58) Field of Classification Search
USPC ... 250/492.1, 492.2, 492.21, 492.22, 492.23, 250/492.3
See application file for complete search history.

(56) References Cited

U.S. PATENT DOCUMENTS

| | | |
|---|---|---|
| 2007/0109511 A1 | 5/2007 | Kelly |
| 2011/0105868 A1 | 5/2011 | Westphal |
| 2011/0292402 A1 | 12/2011 | Awatsuji et al. |
| 2015/0014542 A1* | 1/2015 | Srocka ............... G01N 21/8422 250/341.8 |
| 2016/0120482 A1* | 5/2016 | Kirenko ............... A61B 5/7221 600/479 |
| 2016/0209794 A1* | 7/2016 | Oba ..................... H04N 1/0032 |

FOREIGN PATENT DOCUMENTS

| | | |
|---|---|---|
| JP | H09-329542 A | 12/1997 |
| JP | 2008-064691 A | 3/2008 |
| JP | 2008-157834 A | 7/2008 |
| JP | 2008-175794 A | 7/2008 |
| JP | 2012-235804 A | 12/2012 |
| JP | 2013-228329 A | 11/2013 |
| JP | 2013-228330 A | 11/2013 |
| JP | 2016-053528 A | 4/2016 |
| JP | 2017-156245 A | 9/2017 |
| WO | 2007/038688 A1 | 4/2007 |
| WO | 2010/092739 A1 | 8/2010 |
| WO | 2016/121540 A1 | 8/2016 |

* cited by examiner

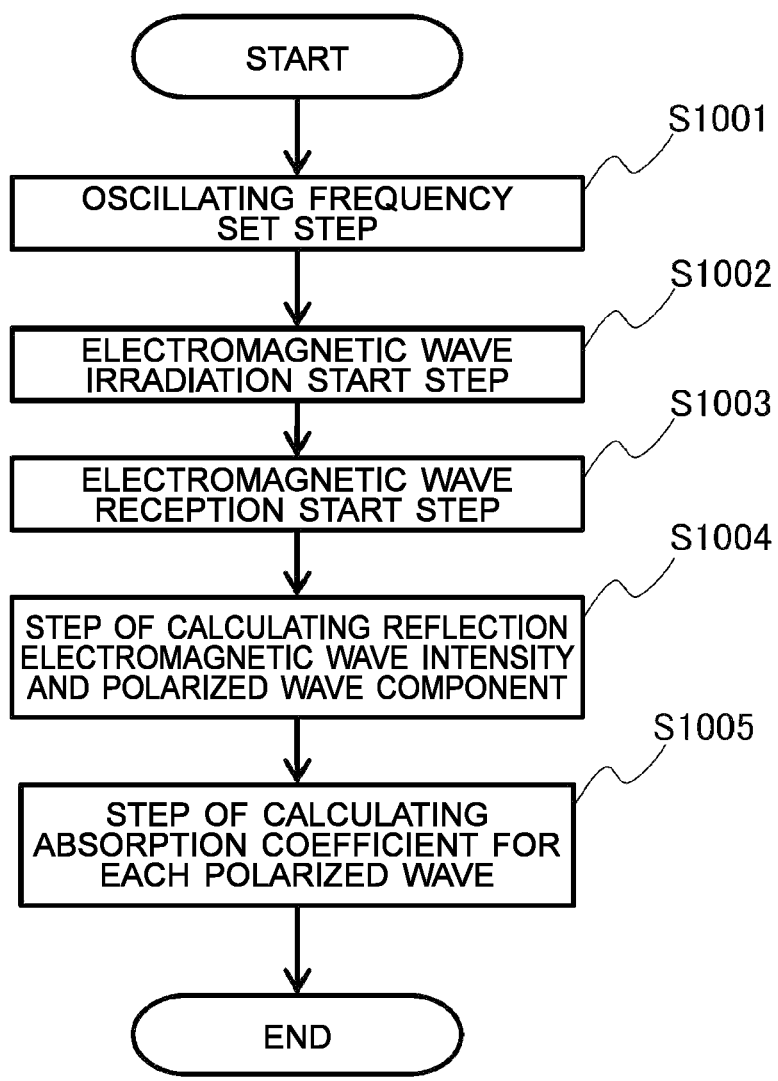

CONTACTLESS INFERNAL MEASUREMENT DEVICE, CONTACTLESS INTERNAL MEASUREMENT METHOD, AND INTERNAL MEASUREMENT RESULT DISPLAY SYSTEM

CROSS-REFERENCE OF RELATED APPLICATIONS

This application is the U.S. National Phase under 35 U.S.C. § 371 of International Patent Application No. PCT/JP2018/037281, filed on Oct. 4, 2018, which in turn claims the benefit of Japanese Patent Application No. 2017-195240, filed on Oct. 5, 2017, the entire disclosures of which Applications are incorporated by reference herein.

TECHNICAL FIELD

The present invention relates to a contactless internal measurement device, a contactless internal measurement method, and an internal measurement result display system.

BACKGROUND ART

Japanese Patent Laid-Open No. 2016-53528 (Patent Literature 1) discloses the background art in the technical field of the present invention. Patent Literature 1 discloses the object to provide "a method of measuring a water content of stratum corneum using terahertz waves", and the solution as "the method of measuring a water content of the stratum corneum according to the present invention includes a process step that brings a skin surface into contact with a prism surface as a terahertz wave emitting surface, and radiates the terahertz waves with the frequency, preferably, equal to or higher than 0.1 THz, and equal to or lower than 3.0 THz to obtain the absorption coefficient using the prism with the refractive index of 2.0 or larger, preferably, 2.5 or larger, and more preferably, 3.0 or larger".

Japanese Patent Publication No. 63-19016 (Patent Literature 2) discloses that "the invention relates to a skin condition measuring method, and more particularly, to the method of measuring the skin corneum condition suitable for estimating lesion of the skin corneum, and effect of application of cream from the moisture content of the skin corneum.", and further discloses that "An object of the present invention is to provide a skin corneum condition measurement method capable of measuring the skin corneum loss (inductance) using high frequency".

CITATION LIST

Patent Literature

PTL 1: Japanese Patent Laid-Open No. 2016-53528
PTL 2: Japanese Patent Publication No. S63-19016

SUMMARY OF INVENTION

Technical Problem

A human skin serves not only to adjust the vital environment and temperature by cutaneous respiration and sweating but also to protect the biological tissue from the external stimulation (foreign substance, bacteria, microbes). It is therefore important to acquire the information on water content in the skin from aspects of health maintenance of heat stroke prevention, and dry skin prevention owing to atopic dermatitis, as well as evaluation of cosmetics and pharmaceutical product, and practical view about the beauty cosmetic article. It is important to observe the daily change in skin by monitoring water contained inside the skin, and skin condition (fineness of skin texture) in view of the above-described aspects.

In the method disclosed in Patent Literature 1, the prism is brought into contact with the measurement subject to allow measurement of the skin moisture content. Upon contact of the prism with the skin (in measurement), there is a possibility of damaging the skin surface. The method as disclosed in Patent Literature 1 cannot measure the condition other than the water content of the stratum corneum.

In the method disclosed in Patent Literature 2, the water content of the stratum corneum is measured focusing on electrical properties of the skin. Therefore, depending on the skin surface condition (for example, in the state where the cosmetic is applied), the flow of electrical current may be blocked or accelerated. The method cannot necessarily provide the accurate measurement value of the stratum corneum of the skin, which only reflects the water content.

That is, in order to measure the internal condition of the measurement subject using the generally employed technology, the measurement in contact with the measurement subject is required. In such a case, the surface of the measurement subject may be influenced and damaged. Upon measurement by utilizing the electrical properties, the surface condition of the measurement subject may hinder the measurement value from being accurate.

It is an object of the present invention to provide a contactless internal measurement device that allows accurate contactless measurement of the internal condition of the measurement subject without influencing the surface state.

Solution to Problem

The present invention relates to a contactless internal measurement device which includes an electromagnetic wave irradiation unit that irradiates an electromagnetic wave to a measurement subject, and an electromagnetic wave receiver that detects the electromagnetic wave reflected by the measurement subject. The electromagnetic wave irradiation unit is disposed to reduce a polarization component of the electromagnetic wave detected by the electromagnetic wave receiver, the polarization component being the same as a polarization component of the electromagnetic wave irradiated by the electromagnetic wave irradiation unit.

Advantageous Effects of Invention

The present invention is capable of accurately measuring the internal condition of the measurement subject in the contactless manner under no influence on the surface condition.

BRIEF DESCRIPTION OF DRAWINGS

FIG. 10 is a flowchart representing an operation for measuring electromagnetic wave intensity and polarization of the inside of the measurement subject using the contactless measurement device according to the second embodiment.

DESCRIPTION OF EMBODIMENTS

Figure 1:
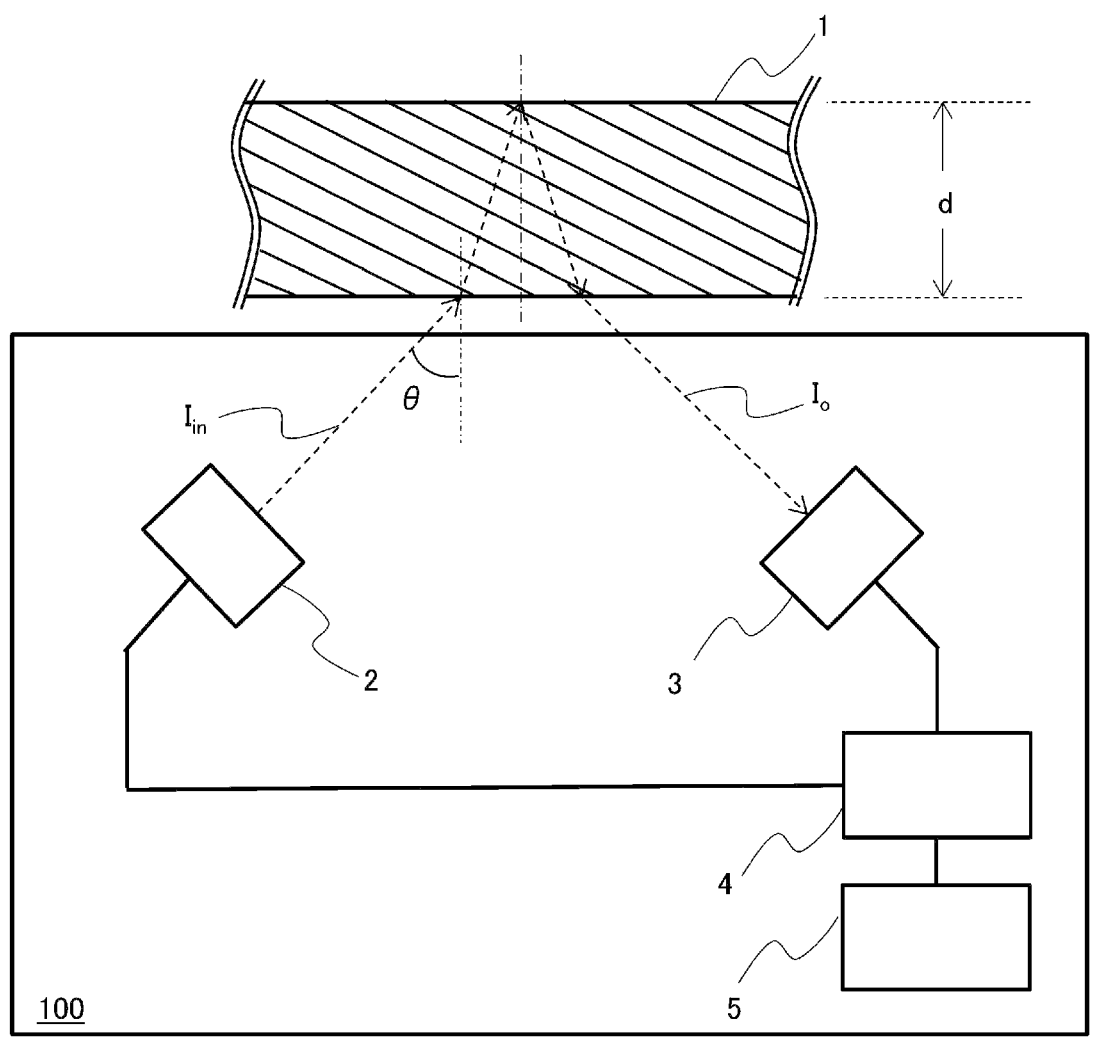
FIG. 1 is a schematic view of a structure of a contactless internal measurement device according to a first embodiment for observing the inside of the measurement subject.

Embodiments of a contactless internal measurement device according to the present invention will be described referring to the drawings. The contactless internal measurement device according to the present invention is configured to accurately measure the internal condition of the measurement subject in a contactless manner using electromagnetic waves in the frequency band peLmeating through the applied makeup, clothing, and plastics. The measurement subject to be measured using the contactless internal measurement device is a human body, for example. The frequency band of the electromagnetic waves used for the contactless internal measurement device is equal to or higher than 10 GHz, and equal to or lower than 30 THz. The contactless internal measurement device according to the present invention is capable of measuring the internal condition of the skin of the human body as the measurement subject in the contactless manner without influencing the skin surface. The contactless internal measurement device according to the present invention allows accurate internal measurement even if the makeup is applied to the skin while suppressing the influence of the surface condition to the measurement result. The contactless internal measurement device according to the present invention is capable of measuring the water content inside the skin, and the rough skin condition while avoiding the influence on the skin surface.

First Embodiment

FIG. 1 is a view showing a structure of a first embodiment of a contactless internal measurement device according to the present invention. As FIG. 1 shows, a measurement device 100 of the embodiment includes a radio transmitter 2 as an electromagnetic wave irradiation unit that emits the electromagnetic wave to irradiate a measurement subject 1, a receiver 3 as an electromagnetic wave receiver that detects the electromagnetic wave reflected by the measurement subject 1, a main controller 4 that controls various operations of the radio transmitter 2 and the receiver 3, and a signal processor 5 that processes the signal of the electromagnetic wave received by the receiver 3.

The measurement subject 1 has its internal condition as the region to be measured. In the embodiment, the thickness of the measurement subject is set to "d", and the human skin is exemplified as the measurement subject.

The electromagnetic wave emitted from the radio transmitter 2 is in the frequency band equal to or higher than 10 GHz, and equal to or lower than 30 THz, for example. The electromagnetic wave at frequency in such range is likely to be absorbed by the internal component of the measurement subject 1. Accordingly, even in the case where the clothing, plastic, makeup or the like intervenes between the radio transmitter 2 and the surface of the measurement subject 1, the electromagnetic wave emitted from the radio transmitter 2 is irradiated to the surface of the measurement subject 1 to reach the inside thereof. An incident angle θ of the electromagnetic wave emitted from the radio transmitter 2 to the measurement subject 1 is adjusted to become the Brewster angle to be described later. As FIG. 1 shows, in the following description, the electromagnetic wave will be indicated by a dashed arrow.

The receiver 3 has a function for detecting the electromagnetic wave reflected from the measurement subject 1. The detection result such as the electromagnetic wave intensity detected by the receiver 3 is notified to the signal processor 5.

The main controller 4 controls operations of the radio transmitter 2 to emit the electromagnetic wave to the measurement subject 1. The main controller 4 controls the operation of the receiver 3 to detect the electromagnetic wave reflected by the measurement object 1. Based on the intensity of the electromagnetic wave detected by the receiver 3, the main controller 4 controls the operation of the signal processor 5 to calculate the measurement result.

Based on the information on the electromagnetic wave intensity detected by the receiver 3, the signal processor 5 calculates the measurement value relevant to the internal condition of the measurement subject 1 under the control of the main controller 4. Each of the main controller 4 and the signal processor 5 may be constituted by a circuit, an MPU (micro processor unit), a CPU (central processor unit), and a circuit that implements functions of the main controller 4 and the signal processor 5, respectively.

The electromagnetic wave irradiated to the measurement subject 1 is the electromagnetic wave of the p-polarized wave (or p-polarized light). When the incident angle e to the boundary surface with different refractive index becomes a predetermined angle, the reflectance of the electromagnetic wave of the p-polarized wave becomes substantially zero. The angle at which the reflectance becomes substantially zero is defined as the "Brewster angle".

Figure 2:
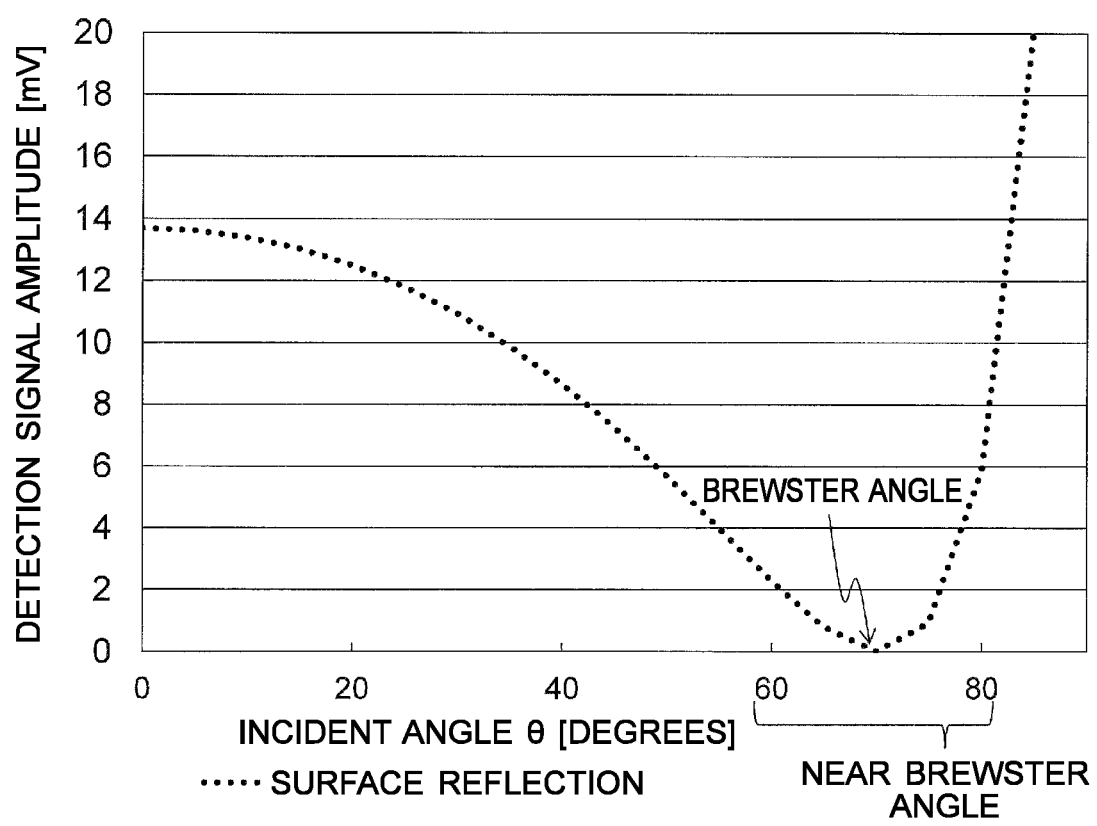
FIG. 2 is a view showing a relation between an incident angle of p-polarized wave and a detection signal amplitude according to the first embodiment.
Figure 3:
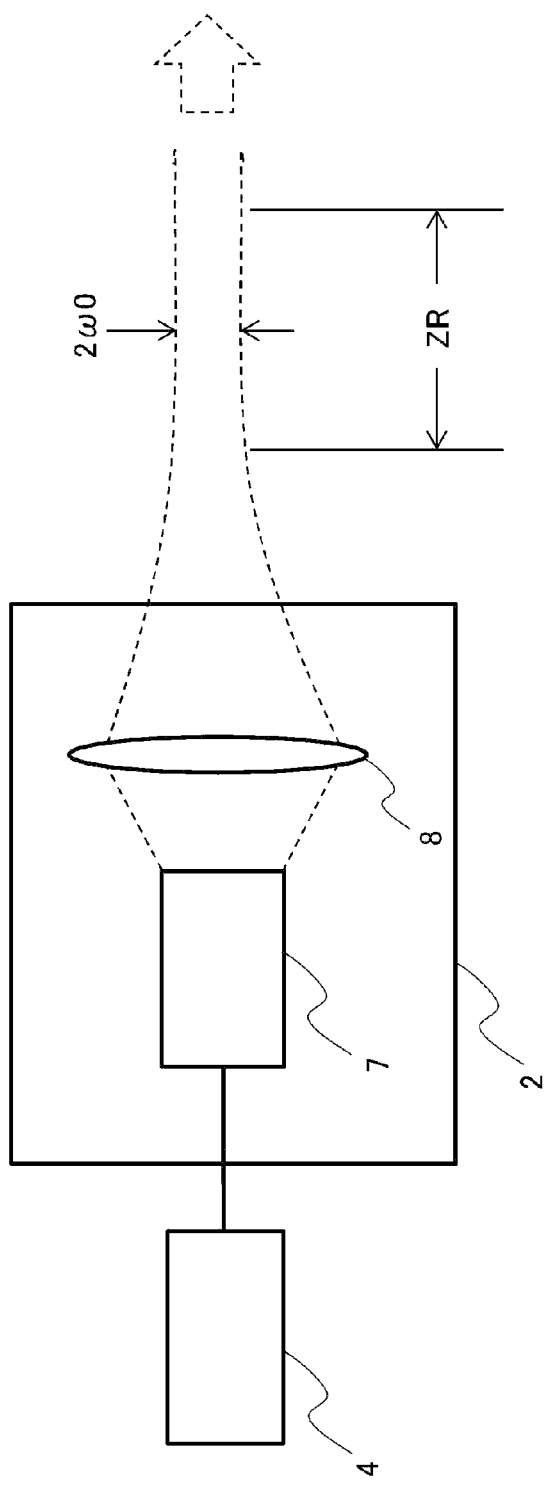
FIG. 3 is a schematic view of an internal structure of a radio transmitter according to the first embodiment.

FIG. 2 is an exemplary graph having an x-axis as the incident angle θ of the electromagnetic wave emitted from the radio transmitter 2, and radiated to the measurement subject 1, and a y-axis as an amplitude of a reception (detection) signal of the electromagnetic wave reflected from the surface of the measurement subject 1, and received by the receiver 3. Since the electromagnetic wave emitted from the radio transmitter 2 is the one of p-polarized wave (or p-polarized light), the incident angle θ exists on the surface of the measurement subject 1 (boundary surface with different refractive index, as the graph in FIG. 3 shows, at which the reflectance of the p-polarized wave becomes substantially zero. Such angle is defined as the "Brewster angle".

The measurement device 100 is configured to adjust the position of the radio transmitter 2 so that the incident angle θ of the electromagnetic wave emitted from the radio transmitter 2, and radiated to the measurement subject 1 becomes the "value near the Brewster angle". The "value near the Brewster angle" refers to the value in a range of ±10° (60° to 80°) assuming that the Brewster angle is 70°.

In the embodiment according to the present invention, the measurement device 100 is configured to adjust the positions of the radio transmitter 2 and the receiver 3 so that the incident angle θ of the electromagnetic wave irradiated to the measurement subject 1 is near the Brewster angle. The electromagnetic wave (p-polarized wave) emitted by the radio transmitter 2 of the measurement device 100 propagates inward in the state where the surface reflection of the measurement subject 1 hardly occurs, and is reflected on the boundary surface of the measurement subject 1, which has the thickness of d. The receiver 3 receives the reflecting electromagnetic wave to be subjected to the signal processing so that the measurement value that reflects the internal condition of the measurement subject 1 is obtained. The measurement device 100 is configured to dispose the electromagnetic generation unit 2 so that the incident angle θ of the electromagnetic wave from the radio transmitter 2 to the measurement subject 1 becomes the Brewster angle. It is therefore preferable to execute sensing of the inside of the measurement subject 1.

In order to receive the electromagnetic wave that has been propagating in the measurement subject 1, and reflecting, the receiver 3 is disposed so that the angle that refracts on the surface of the measurement subject 1 is near the Brewster angle.

The intensity of the electromagnetic wave emitted by the radio transmitter 2 is designated as an emission electromagnetic wave intensity $I_{in}$, and a coefficient at which the electromagnetic wave is absorbed and attenuated by the internal component of the measurement subject 1 is designated as an absorption coefficient $\alpha_0$. In this case, a reflection electromagnetic wave intensity $I_0$ reflected from the inside of the measurement subject 1 with thickness of d may be derived from a formula 1 as follows.

[formula 1]

$$I_0 = I_{in} \times \exp(-2\alpha_0 \cdot d) \qquad \text{(formula 1)}$$

The measurement device 100 is intended to measure the absorption coefficient $\alpha_0$ of the measurement subject 1. In the formula 1, the thickness d of the measurement subject 1 is not necessarily known. Therefore, it is not possible to calculate the absorption coefficient $\alpha_0$ based on the electromagnetic wave intensity unless the thickness d of the measurement subject 1 is specified. However, when observing the change in the monitored condition of the measurement subject 1 (or time), the thickness d of the measurement subject 1 may be regarded as a fixed value that is kept unchanged. Even when monitoring the different measurement subject 1, it may be handled in the similar manner to the case where the thickness d of the measurement subject 1 is kept unchanged by setting the time change rate of the measurement value and the deviation of the measurement value for each measurement time through preliminary management of the measurement subject. Regarding the "$\alpha_0 \cdot d$" as the new teLin "$\alpha'$", the formula 1 may be modified into a formula 2 as below.

[formula 2]

$$\alpha' = \alpha_0 \cdot d = -\frac{1}{2} \times 10 \ln\left(\frac{I_o}{I_{in}}\right) \quad \text{(formula 2)}$$

Referring to the formula 2, measurement of the emission electromagnetic wave intensity $I_{in}$ of the electromagnetic wave emitted from the radio transmitter 2, and the reflection electromagnetic wave intensity $I_o$ of the electromagnetic wave received by the receiver 3 allows calculation of the absorption coefficient $\alpha_0$ of the measurement subject 1 readily as an absorption coefficient $\alpha'$. The measurement device 100 is operated to calculate the absorption coefficient $\alpha'$ so that the contactless measurement of the internal condition of the measurement subject 1 is executable.

The internal structure of the radio transmitter 2 of the measurement device 100 according to the first embodiment will be described. FIG. 3 is a view showing an example of an internal structure of the radio transmitter 2. As FIG. 3 shows, an electromagnetic wave generator 7 and at least one lens 8 are provided in the radio transmitter 2. The electromagnetic wave generator 7 emits and stops emission of the electromagnetic wave at a predeteLlnined frequency under the control of the main controller 4. It is possible to use, for example, a Gunn diode, an IMPATT diode, a TUNNETT diode, a resonant tunnel diode, and the like for the electromagnetic wave generator 7.

The lens 8 is formed so that the electromagnetic wave emitted from the electromagnetic wave generator 7 has the beam waist radius of $\omega_0$. Since the measurement device 100 is not in contact with the measurement subject 1, there is a possibility that the distance between the radio transmitter 2 and the surface of the measurement subject 1 during the measurement is instable. It is therefore necessary to prevent unevenness in the measurement value under the influence of instability. Assuming that the wavelength of the electromagnetic wave emitted from the electromagnetic wave generator 7 is $\lambda$, a region $Z_R$ that can be regarded as substantially parallel electromagnetic wave is expressed by a formula 3 below.

[formula 3]

$$Z_R = \frac{\pi \omega_0^2}{\lambda} \quad \text{(formula 3)}$$

As the formula 3 clearly shows, the electromagnetic wave irradiated to the measurement subject 1 scatters in square relation with (square of) the beam waist radius $\omega_0$ of the electromagnetic wave emitted from the electromagnetic wave generator 7. The sensitivity of the measurement result to the displacement of the distance may be reduced for coping with the variable distance displacement between the measurement device 100 and the measurement subject 1 for each measurement. The above-described problem may be solved by making the beam waist radius $\omega_0$ large to a certain extent.

Assuming that the beam waist is set to 1 cm, and the frequency of the electromagnetic wave emitted from the radio transmitter 2 is set to 0.1 THz (100 GHz), the region $Z_R$ becomes 10.5 cm from the formula 3. In this case, the electromagnetic wave in the range of 10.5 cm from the measurement surface of the measurement subject 1 may be regarded as substantially parallel electromagnetic wave. Accordingly, the distance between the measurement device 100 and the surface of the measurement subject 1 may be 10.5 cm or smaller. When executing the measurement while holding the portable measurement device 100 to keep the distance from the measurement subject 1 within 10.5 cm or smaller, the device may be used in the range where the irradiated electromagnetic wave is regarded as being parallel. When measuring the skin condition while having the measurement device 100 held by the hand, it is possible to reduce the sensitivity of the measurement result to the distance displacement in the focusing direction caused by the hand shake.

Figure 4:
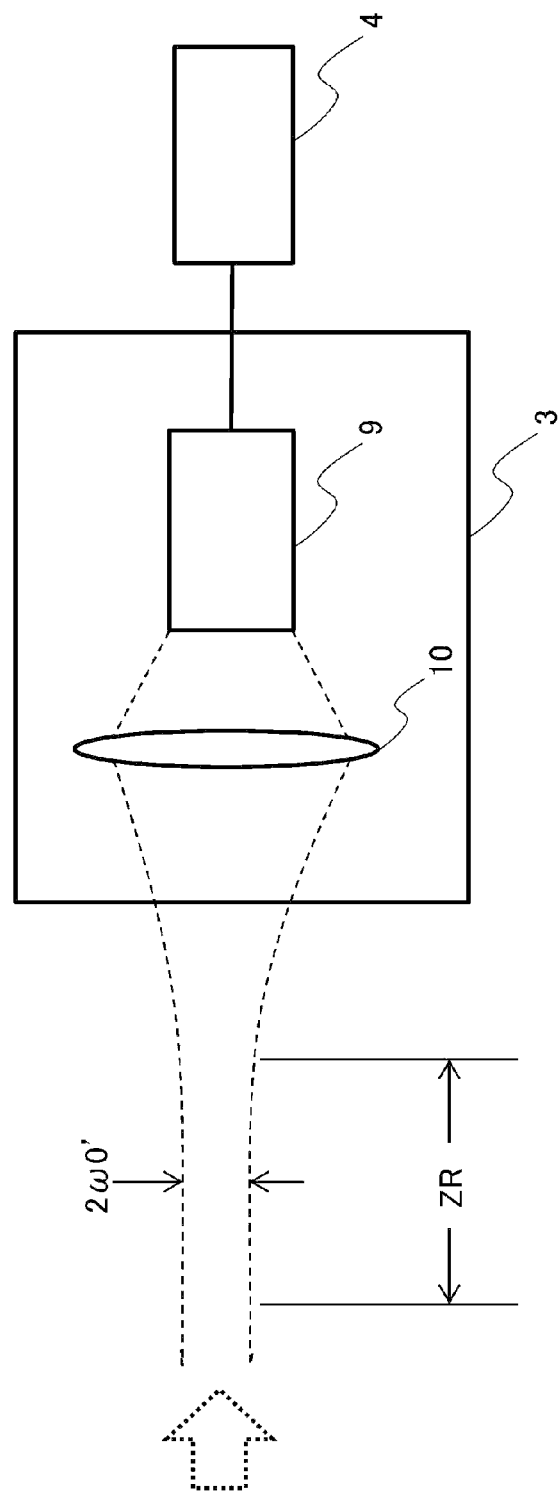
FIG. 4 is a schematic view of an internal structure of a receiver according to the first embodiment.

An internal structure of the receiver 3 of the measurement device 100 according to the embodiment will be described. FIG. 4 is a view showing an example of the internal structure of the receiver 3. As FIG. 4 shows, the receiver 3 includes a radio detector 9 and a lens 10. The radio detector 9 receives and stops reception of the electromagnetic wave under the control of the main controller 4. The lens 10 serves to condense the electromagnetic wave on the surface of the radio detector 9. It is possible to use, for example, a Schottky barrier diode, a resonant tunnel diode, a high mobility transistor (HEMT), a hetero barrier diode, a carbon nanotube, and the like for the radio detector 9.

Figure 5A:
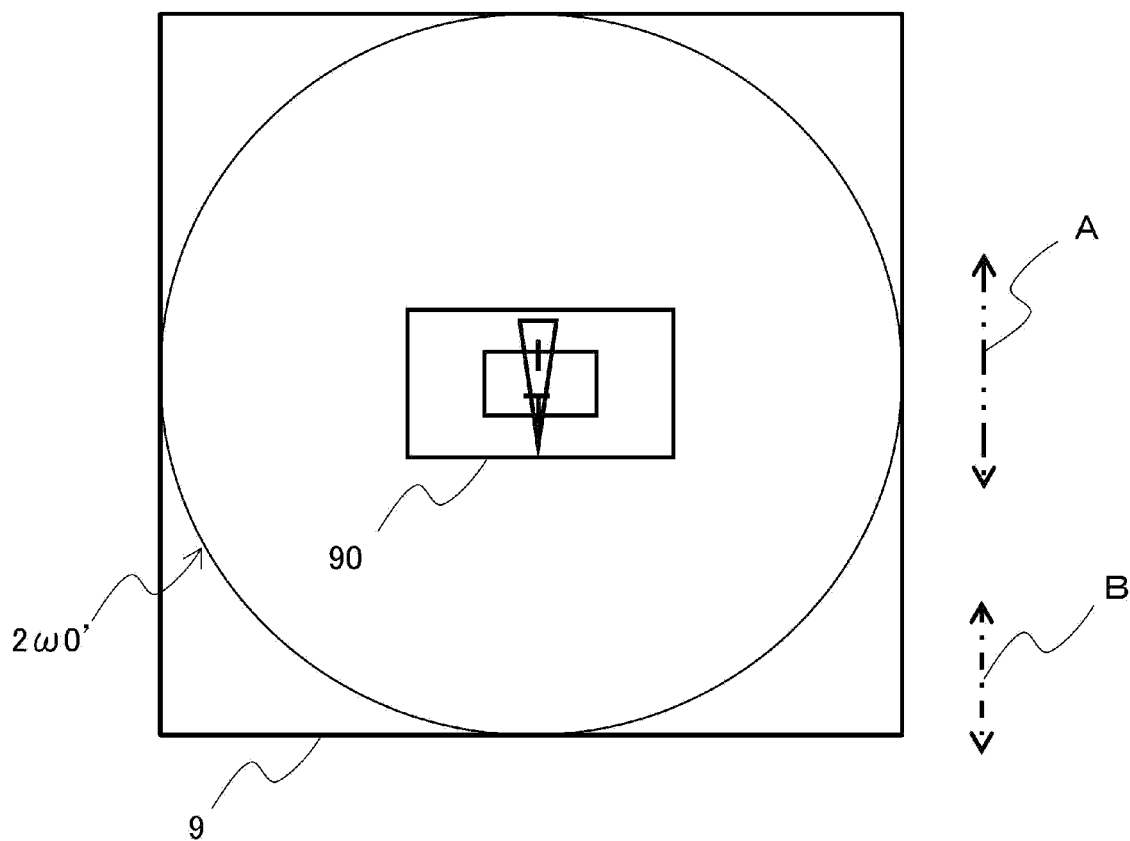
FIG. 5A is a schematic view showing an example of the receiver constituted by one light receiver element according to the first embodiment.
Figure 5B:
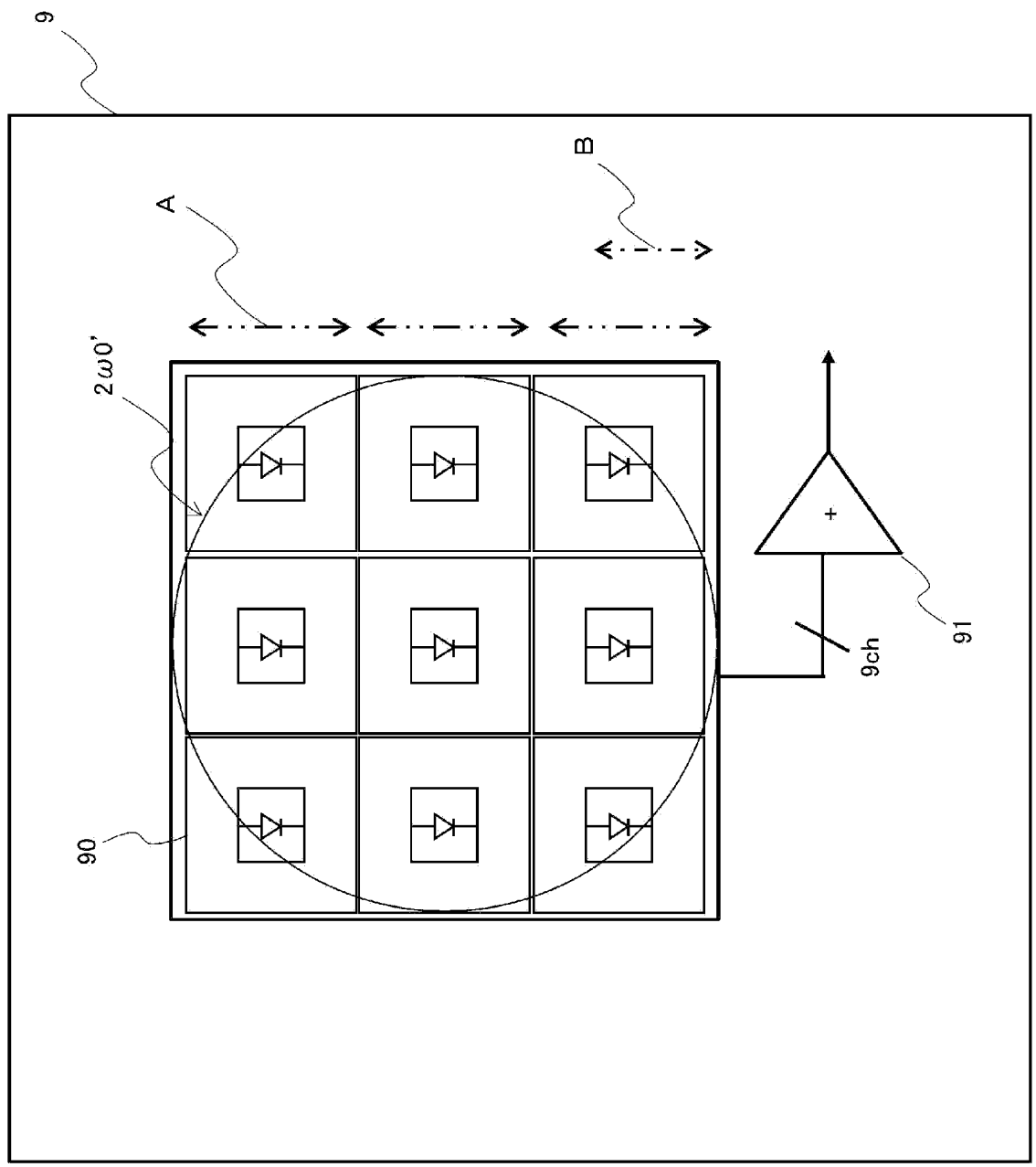
FIG. 5B is a schematic view showing an example of the receiver constituted by a plurality of light receiver elements according to the first embodiment.

An example of the internal structure of the radio detector 9 according to the first embodiment will be described. FIG. 5A shows an example that the radio detector 9 according to the first embodiment is constituted by one receiver element 90. FIG. 5B shows an example that the radio detector 9 according to the first embodiment is constituted by a plurality of receiver elements 90. Each two-dotted chain line arrow A shown in FIGS. 5A and 5B is exemplified as a polarizing direction of the electromagnetic wave that can be received by the receiver element 90. Similarly, each dotted chain line arrow B is exemplified as a polarization direction of the electromagnetic wave that has been emitted from the radio transmitter 2.

Referring to an example of the structure of FIG. 5A, when the electromagnetic wave formed to have the beam waist radius of $\omega_0$ is reflected by the measurement subject 1, and received by the radio detector 9, the detection signal is derived from the single receiver element 90 to the beam waist radius $\omega_0'$. Referring to an example of the structure of FIG. 5B, detection signals of the plurality of planarly arranged receiver elements 90 to the beam waist radius $\omega_0'$ are added by an adder 91 so that the detection signal equivalent to the total of the respective detection signals is obtained. The radio detector 9 serves as an electromagnetic wave detector.

As described using the formula 3, the resolution measurable by the measurement device 100 is determined by the wavelength $\lambda$ of the electromagnetic wave emitted by the radio transmitter 2. If the radio detector 9 is small for the beam waist radius $\omega_0'$, the receiver element 90 is disposed inside the beam waist radius $\omega_0'$ on the reception surface for receiving the electromagnetic wave.

As FIG. 5B shows, the radio detector 9 may be constituted by arranging a plurality of receiver elements 90 on the electromagnetic wave reception surface. Each of the receiver elements 90 is disposed inside the circle with the diameter equivalent to the beam waist ($2\omega_0'$). The detection signal may be derived from summing the detection signals of the respective receiver elements 90. This makes it possible to enlarge the electromagnetic wave reception area to improve the signal component of the signal to noise ratio.

Figure 6A:
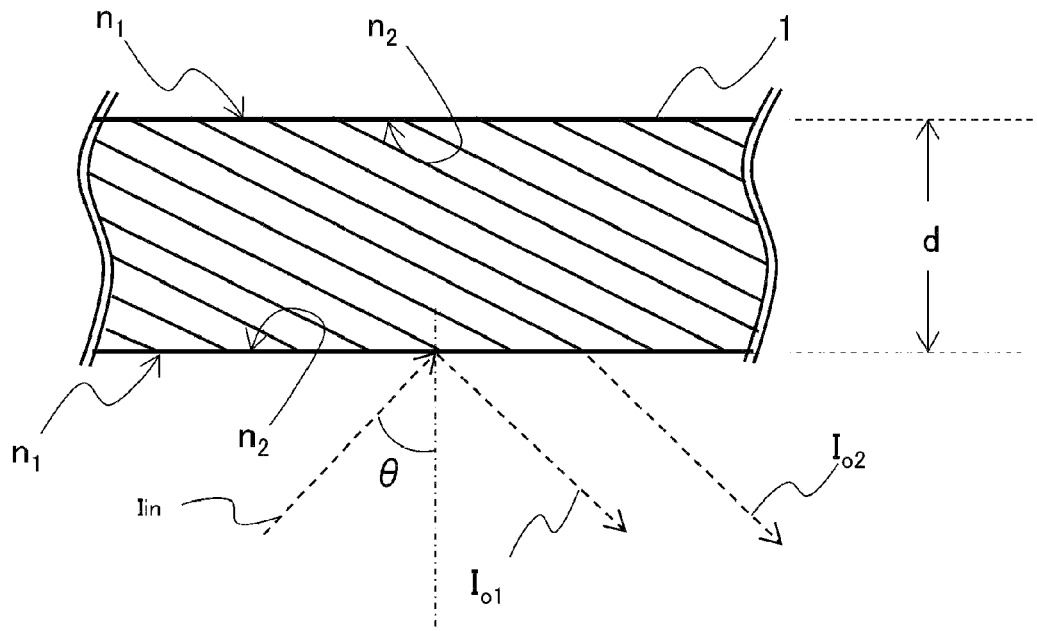
FIG. 6A is a schematic view of the measurement subject of the first embodiment.
Figure 6B:
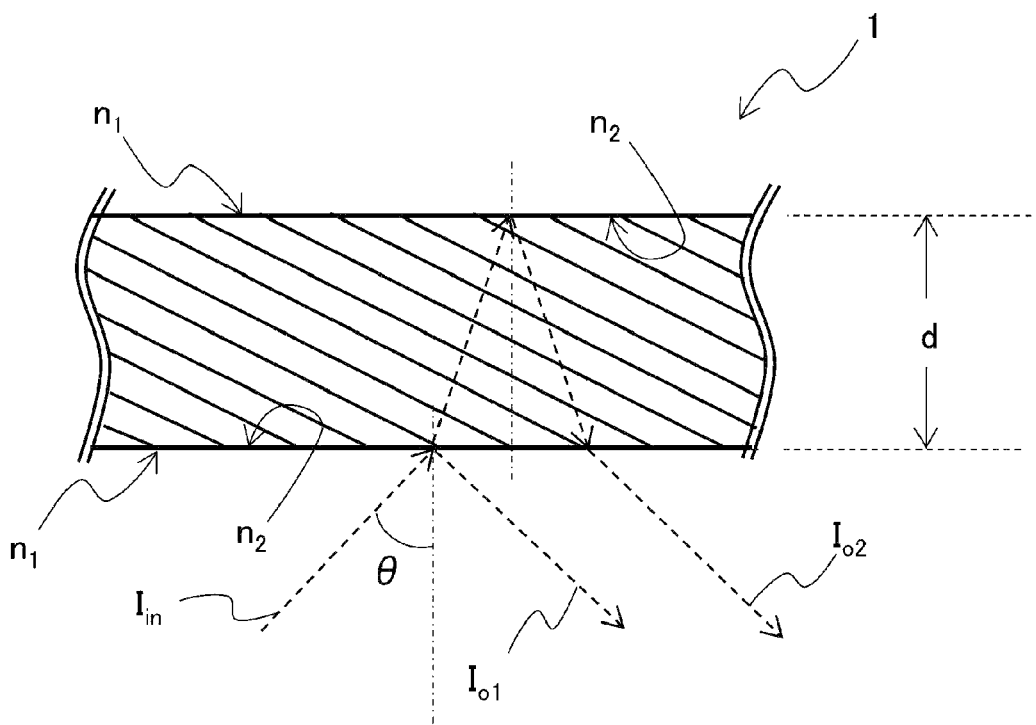
FIG. 6B is a schematic view showing a propagation process of the electromagnetic wave in the measurement subject of the first embodiment.

FIG. 6A schematically shows an example of the measurement subject 1. FIG. 6B schematically shows an example of the propagation process of the electromagnetic wave inside the measurement subject 1 in more detail. In this case, the refractive index of the measurement subject 1 is designated as "$n_1$", and a double refractive index of the measurement subject 1 is designated as "$n_2$".

As FIG. 6A shows, the electromagnetic wave reflected by the interface (interface between the refractive index $n_1$ and the double refractive index $n_2$) at the incident surface side of the measurement subject 1 has a reflection electromagnetic wave intensity $I_{o1}$ and a reflection electromagnetic wave intensity $I_{o2}$. As FIG. 6B shows, the reflection electromagnetic intensity $I_{o1}$ refers to the intensity of the electromagnetic wave reflected by the interface between the refractive index $n_1$ and the double refractive index $n_2$. The reflection electromagnetic wave intensity $I_{o2}$ refers to the intensity of the electromagnetic wave that has been permeating through the interface with the refractive index $n_1$, propagating inside the measurement subject 1, and reflected by the interface (interface between the double refractive index $n_2$ and the refractive index $n_1$) of the measurement subject 1 at the back surface side. The measurement subject 1 has the thickness "d".

Assuming that the incident angle $\theta 0$ is the Brewster angle, the reflection electromagnetic wave intensity $I_{o1}$ upon reflection by the surface of the measurement subject 1 may be regarded as substantially zero. That is, the electromagnetic wave to be received by the receiver 3 may be regarded to have the intensity (reflection electromagnetic wave intensity $I_{o2}$) of the scattered electromagnetic wave absorbed and scattered inside the measurement subject 1. Accordingly, the arithmetic operation is executed based on the formula 2 to calculate the absorption coefficient $\alpha'$ of the measurement subject 1. Based on the absorption coefficient $\alpha'$, the internal condition of the measurement subject 1 may be measured.

Figure 7:
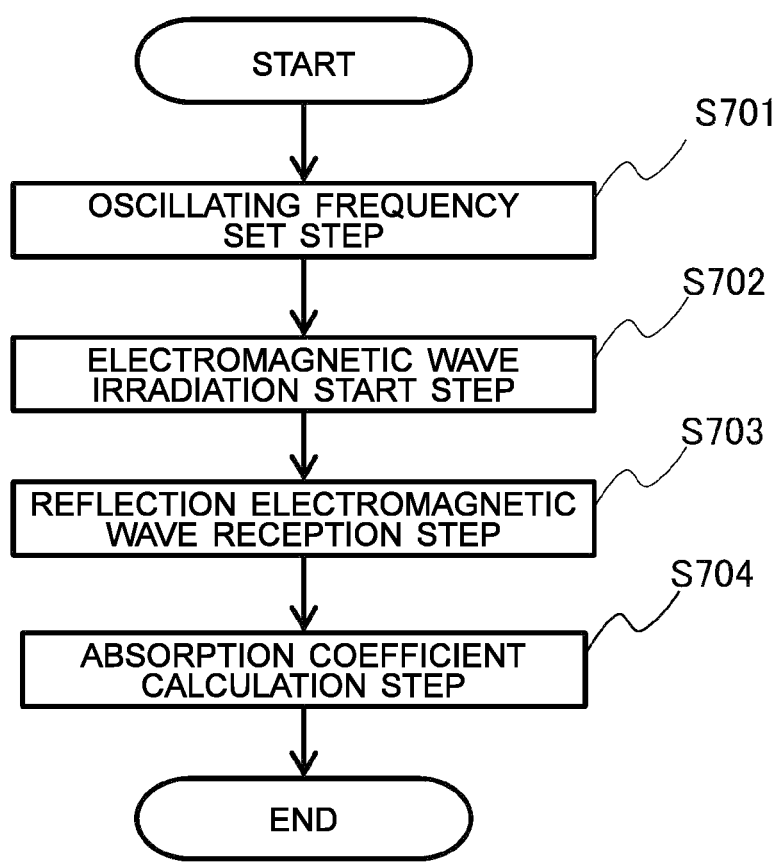
FIG. 7 is a flowchart representing an operation of electromagnetic wave intensity measurement to be performed by a contactless internal measurement device according to the first embodiment.

The operation flow of the measurement device 100 will be described referring to the flowchart of FIG. 7. The flowchart to be described in the specification represents an embodiment of the contactless internal measurement method according to the present invention. The respective process steps according to the embodiment are implemented by the main controller 4 of the measurement device 100 that executes the computer program utilizing hardware resources.

The main controller 4 executes a frequency set step to allow the electromagnetic wave generator 7 to generate the electromagnetic wave at a predetermined frequency (S701). The frequency suitable for the internal measurement varies depending on the difference in the internal component of the measurement subject 1. Accordingly, the frequency suitable for the measurement of the internal component of the measurement subject 1 may be arbitrarily set.

The main controller 4 executes an electromagnetic wave irradiation start step to allow the radio transmitter 2 to irradiate the measurement subject 1 with the electromagnetic wave with predetermined intensity at the predetermined frequency (S702). In S702, the radio transmitter 2 emits the electromagnetic wave with the emission electromagnetic wave intensity $I_{in}$.

The main controller 4 executes an electromagnetic wave reception start step to allow the receiver 3 to start reception of the electromagnetic wave (S703). In S703, the plurality of radio detectors 9 receive the electromagnetic wave reflected from the measurement subject 1 to acquire the detection signal equivalent to the sum of the reflection electromagnetic wave intensity $I_{o1}$ and the reflection electromagnetic wave intensity $I_{o2}$.

Using the total sum of the detection signals calculated by the receiver 3 and the emission electromagnetic wave intensity $I_{in}$ of the electromagnetic wave emitted from the radio transmitter 2, the signal processor 5 executes an absorption coefficient calculation step that calculates the absorption coefficient $\alpha'$ of the measurement subject 1 (S704).

Execution of the above-described process steps allows measurement of the value indicating the internal condition of the measurement subject 1 using the measurement device 100 at a certain time. For example, if water constitutes the inside of the measurement subject 1, the absorption coefficient $\alpha'$ has no peak even when irradiating the electromagnetic wave at an arbitrary frequency in the range equal to or higher than 10 GHz, and equal to or lower than 30 THz. That is, if water constitutes the inside of the measurement subject 1, the arbitrary frequency has the broad spectrum in the frequency band from 10 GHz or higher to 30 THz or lower. Therefore, the water content may be detected at any frequency to be set in S701 in the above-described range. In this case, compared with the past measurement values, it is preferable to set the same frequency as the one in the past case. Assuming that the past measurement result is stored in the main controller 4, the change in the water content may be calculated after execution of S704.

Assuming that water vapor constitutes the inside of the measurement subject 1, the absorption coefficient $\alpha'$ has the peak depending on the frequency of the electromagnetic wave. Specifically, it is known that the absorption coefficient $\alpha'$ has the peak at the frequency of 0.56 THz or 0.75 Hz. Accordingly, in the case where it is preliminarily known that the water vapor constitutes the inside of the measurement subject 1, the frequency may be set to 0.56 THz or 0.75 Hz as the frequency to be set for the electromagnetic wave generator 7 under the control of the main controller 4 in S701.

The present invention is not limited to the embodiment as described above, but includes various modifications. For example, the embodiment is described in detail for readily understanding of the present invention which is not necessarily limited to the one equipped with all structures as described above. It is possible to replace a part of the structure of one embodiment with the structure of another embodiment. The one embodiment may be provided with an additional structure of another embodiment. It is further possible to add, remove, and replace another structure to, from and with a part of the structure of the respective embodiments. In the embodiment, the refractive index inside the measurement subject 1 is exemplified as the double refractive index $n_2$. The refractive index with no absorption coefficient may be applied to the similar structure. It is possible to generate the p-polarized wave using the polarization element (filter and the like) as the polarized wave of the electromagnetic wave irradiated from the radio transmitter 2 to the measurement subject 1.

Second Embodiment

A second embodiment of the contactless internal measurement device according to the present invention will be described. This embodiment is different from the above-described first embodiment in that the radio detector 9 has a structure capable of acquiring the polarized wave (or polarized light) info mation relating to the polarization component in at least two directions including the polarization direction (perpendicular direction) perpendicular to the polarization direction of the electromagnetic wave irradiated to the measurement subject 1. Other structures are similar to those of the first embodiment. In this embodiment, the difference from the first embodiment will be described. In this embodiment, the p-polarized wave as the electromagnetic wave is irradiated from the radio transmitter 2 to the measurement subject 1.

Figure 8A:
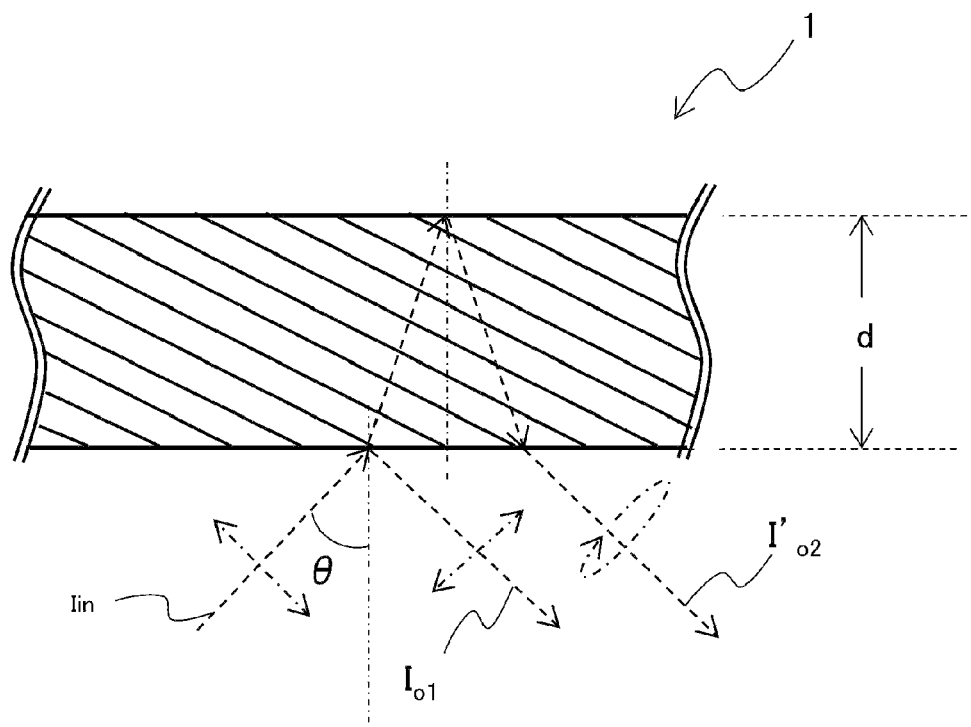
FIG. 8A is a schematic view showing an inside of a measurement subject of a second embodiment.
Figure 8B:
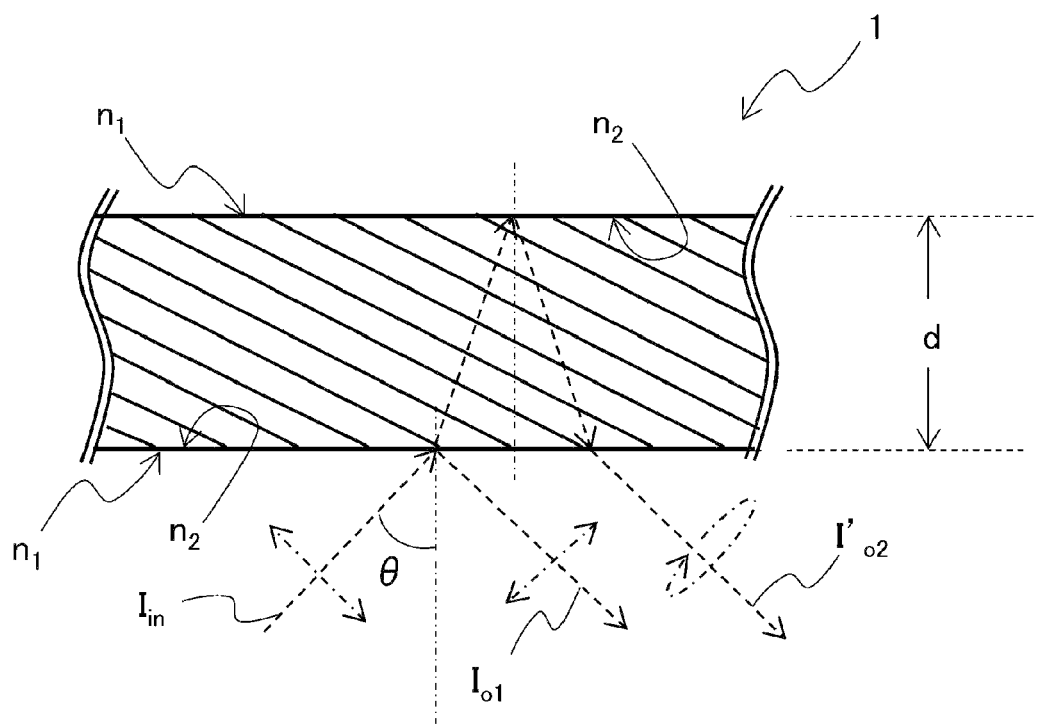
FIG. 8B is a schematic view showing a propagation process of the electromagnetic wave in the measurement subject of the second embodiment.

FIG. 8A schematically shows an example of the measurement subject 1 according to the second embodiment. FIG. 8B schematically shows the propagation process of the electromagnetic wave inside the measurement subject 1 in more detail in consideration of the polarized wave (polarized light) direction. As FIGS. 8A and 8B show, the refractive index of the measurement subject 1 is designated as "$n_1$", and the double refractive index of the measurement subject 1 is designated as "$n_2$". In FIG. 8, the polarization direction of the electromagnetic wave is clearly indicated by a dotted chain line arrow.

Focusing on each polarization component of the electromagnetic waves with the reflection electromagnetic wave intensities $I_{o1}$ and $I'_{o2}$, the p-polarized wave is kept in the polarization component of the reflection electromagnetic wave intensity $I_{o1}$. Meanwhile, the polarization component of the reflection electromagnetic wave intensity $I'_{o2}$ is changed by the propagation inside the measurement subject 1 with the double refractive index. In the structure as described in the first embodiment, if the incident angle θ of the electromagnetic wave to be irradiated deviates from the Brewster angle, the reflection electromagnetic wave intensity $I_{o1}$ is detected by the receiver 3. The robustness to the "deviation" from the Brewster angle may be improved by detecting the polarized wave (p-polarized wave) of the electromagnetic wave with reflection electromagnetic wave intensity $I_{O1}$ reflected by the surface of the measurement subject 1, and the change in the polarized wave owing to the internal component using the polarization component information. The detection as described above allows extraction only of the detection signal derived from the reflection electromagnetic wave intensity $I'_{o2}$ independent of the reflection electromagnetic wave intensity $I_{o1}$.

Figure 9A:
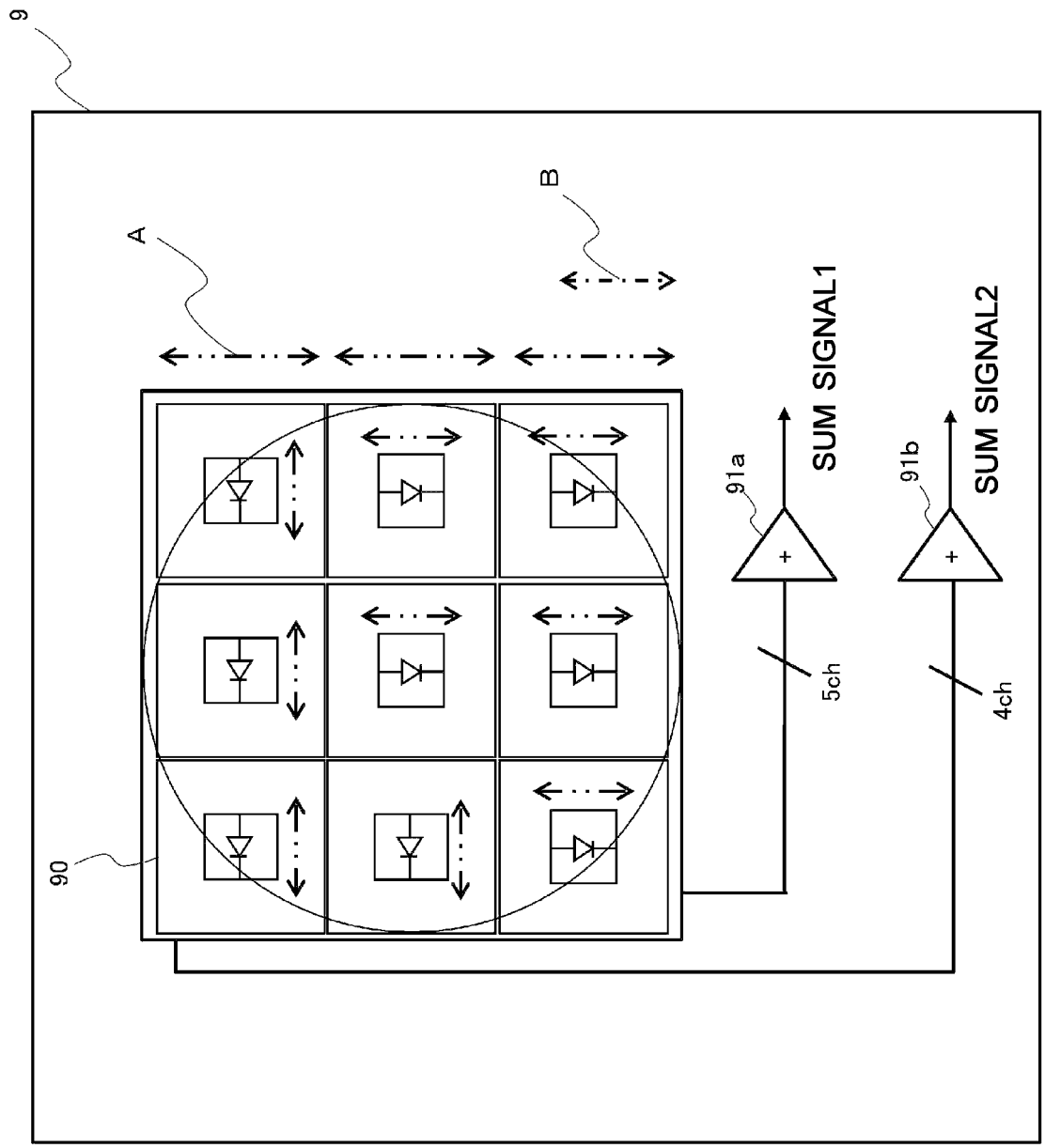
FIG. 9A is a schematic view showing an exemplary structure of a radio detector according to the second embodiment.
Figure 9B:
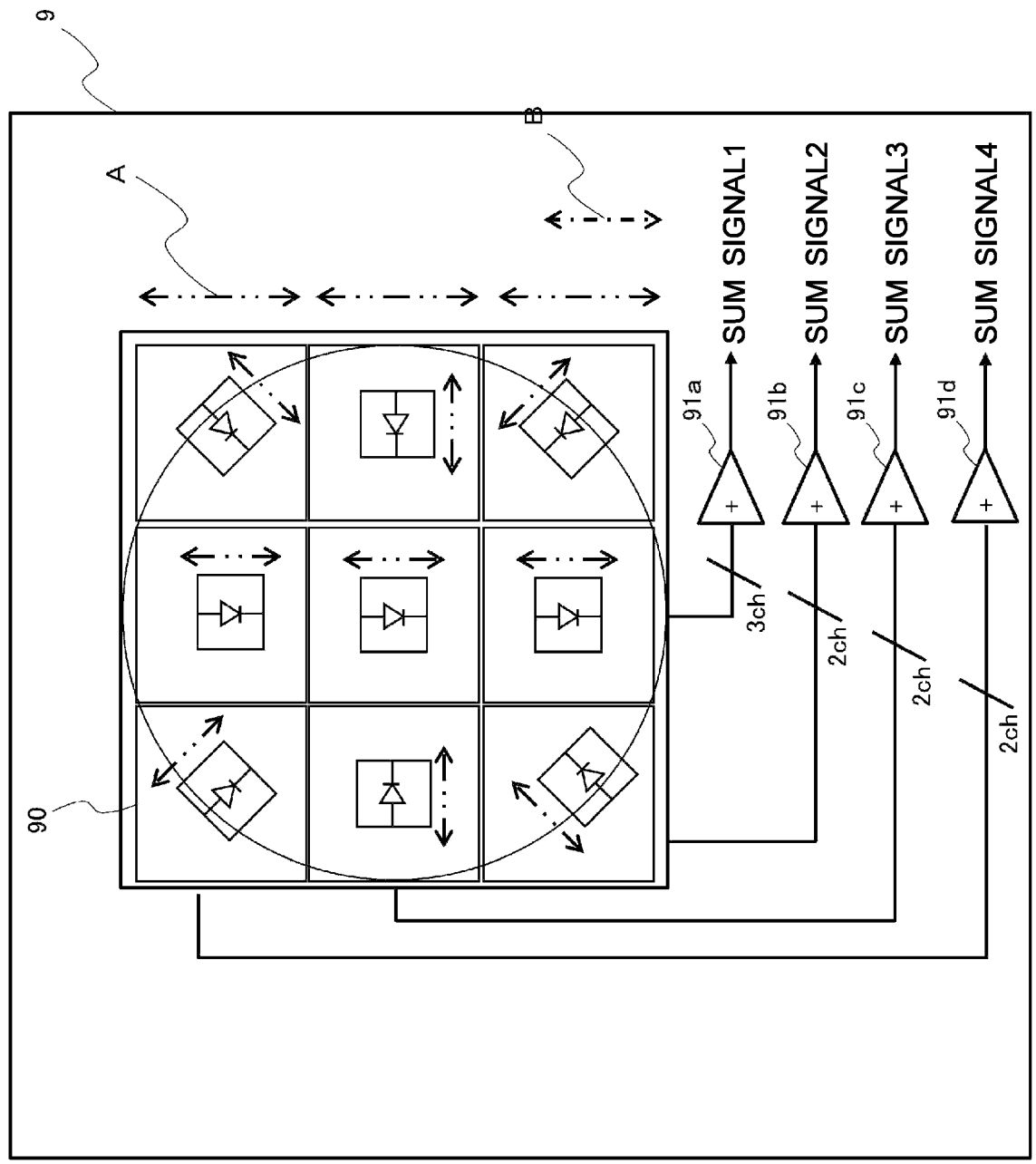
FIG. 9B is a schematic view showing another exemplary structure of the radio detector according to the second embodiment.

The internal structure of the radio detector 9 that allows the measurement according to the embodiment will be described referring to FIG. 9. FIG. 9A shows an example of the radio detector 9 constituted by a plurality of planarly arranged receiver elements 90. FIG. 9B shows another example of the radio detector 9 constituted by the plurality of planarly arranged receiver elements 90. Each two-dotted chain line arrow A shown in FIGS. 9A and 9B is exemplified as a polarization direction of the electromagnetic wave that can be received by the receiver element 90. Similarly, each dotted chain line arrow B is exemplified as a polarization direction of the electromagnetic wave that has been emitted from the radio transmitter 2.

Referring to the structure shown in FIG. 9A, the receiver elements 90 are disposed to detect the electromagnetic wave with the same polarization as that of the electromagnetic wave emitted from the radio transmitter 2, and the electromagnetic wave turned at 90° to the polarization. Referring to the structure shown in FIG. 9B, the receiver elements 90 are disposed to detect the electromagnetic wave with the same polarization as that of the electromagnetic wave emitted from the radio transmitter 2, the electromagnetic wave turned at 90° to the polarization, and the electromagnetic wave turned at ±45° to the polarization. In the example as shown in FIG. 9B, the receiver elements 90 are radially arranged.

The radio detector 9 as shown in FIGS. 9A and 9B includes an adder 91 that adds the detection signal from the receiver element 90 in the same polarization direction. The structure as shown in FIG. 9A includes an adder 91a and an adder 91b. The adder 91a outputs a sum of detection signals of five receiver elements 90 for detecting the same polarization as the electromagnetic wave irradiated from the radio transmitter 2 to the measurement subject 1. The adder 91b outputs a sum of the detection signals from four receiver elements 90 for detecting the electromagnetic waves turned at 90° to the polarization of the electromagnetic wave irradiated from the radio transmitter 2 to the measurement subject 1.

The radio detector 9 according to the embodiment allows extraction only of the detection signal of the reflection electromagnetic wave intensity $I'_{o2}$ independent of the reflection electromagnetic wave intensity $I_{o1}$ using a sum signal 1 output from the adder 91a and a sum signal 2 output from the adder 91b. In this case, the number of the receiver elements 90 used for detecting the respective polarizations is not limited to the number as described above, but may be determined so that a specific polarization is only detected from the measurement subject 1.

Referring to the structure as shown in FIG. 9B, the radio detector 9 includes adders 91a, 91b, 91c, and 91d. The adder 91a outputs the sum signal 1 as the sum of the detection signals of three receiver elements 90 for detecting the same polarization as that of the electromagnetic wave irradiated from the radio transmitter 2 to the measurement subject 1. The adders 91b and 91c output the sum signal 2 and a sum signal 3, respectively each as the sum of the detection signals of two receiver elements 90 in the respective directions for detecting the electromagnetic waves turned at ±45° to the polarization of the electromagnetic wave irradiated from the radio transmitter 2 to the measurement subject 1. The adder 91d outputs a sum signal 4 as a sum of the detection signals of two receiver elements 90 for detecting the electromagnetic waves turned at 90° to the polarization of the electromagnetic wave irradiated from the radio transmitter 2 to the measurement subject 1.

The radio detector 9 of the embodiment allows extraction only of the detection signal of the reflection electromagnetic wave intensity $I'_{o2}$ independent of the reflection electromagnetic intensity $I_{o1}$ using the sum signals 1, 2, 3, 4. In this case, the number of the receiver elements 90 used for detecting the respective polarizations is not limited to the number as described above, but may be determined so that a specific polarization is only detected from the electromagnetic waves reflected from the measurement subject 1. This makes it possible to measure the p-polarized wave with the reflection electromagnetic wave intensity $I_{o1}$, and the other reflection electromagnetic wave intensity among the signals received by the receiver 3 for each polarization.

An operation flow of the measurement device 100 according to the embodiment will be described referring to the flowchart of FIG. 10. The main controller 4 executes a frequency set step to allow the electromagnetic wave generator 7 to generate the electromagnetic wave at the prescribed frequency (S1001). The frequency suitable for the internal measurement varies in accordance with the difference in the internal component of the measurement subject 1. Accordingly, the frequency suitable for the internal measurement of the internal component of the measurement subject 1 may be arbitrarily set.

The main controller 4 executes an electromagnetic wave irradiation start step to allow the radio transmitter 2 to irradiate the electromagnetic wave with emission electromagnetic wave intensity $I_{in}$ at the prescribed frequency to the measurement subject 1 (S1002).

Then the main controller 4 executes an electromagnetic wave reception start step to allow the receiver 3 to start reception of the electromagnetic wave (S1003). In S1003, based on the intensities (reflection electromagnetic wave intensities $I_{o1}$ and $I_{o2}$) of the electromagnetic waves received by the respective radio detectors 9, the above-described sum signals 1 to 4 are calculated.

A step of calculating reflection electromagnetic wave intensity and polarization component is executed (S1004) to allow the signal processor 5 to calculate the reflection electromagnetic intensity $I'_{o1}$ or $I'_{o2}$ of the electromagnetic wave for each polarization from the sum signal calculated in S1003 to obtain the polarization component for each polarization.

Then absorption coefficient calculation step is executed (S1005) to allow the signal processor 5 to calculate the absorption coefficient α' for each polarized light based on the electromagnetic wave intensity for each polarized light that has been calculated in S1004.

Execution of the above-described steps allows measurement of the value indicating the internal condition of the measurement subject 1 at a specific time using the measurement device 100. For example, if water is contained in the measurement subject 1, when irradiating the electromagnetic wave at an arbitrary frequency from 10 GHz or higher to 30 THz or lower, the absorption coefficient α' has no peak. If water constitutes the inside of the measurement subject 1, an arbitrary frequency ranging from 10 GHz or higher to 30 THz or lower has the broad spectrum. Accordingly, the frequency may be set to the value in the above-described range in S1001. In this case, compared with the past measurement value, it is preferable to set the same frequency as the one used in the past. Assuming that the past measurement result is stored in the main controller 4, it is possible to measure change in the water content, or skin roughness (instable polarization direction) after execution of S1005.

The present invention is not limited to the embodiments as described above, but includes various modifications. For example, the embodiment is described in detail for readily understanding of the present invention which is not necessarily limited to the one equipped with all structures as described above. It is possible to replace a part of the structure of one embodiment with the structure of another embodiment. The one embodiment may be provided with an additional structure of another embodiment. It is further possible to add, remove, and replace another structure to, from and with a part of the structure of the respective embodiments. In the embodiment, the refractive index inside the measurement subject 1 is exemplified as the double refractive index $n_2$. The refractive index with no absorption coefficient may be applied to the similar structure.

In order to improve robustness to the Brewster angle, the receiver elements 90 may be arranged to detect the electromagnetic wave turned at 90° to polarization of the electromagnetic wave emitted from the radio transmitter 2. In this embodiment, the number of the receiver elements 90 is set to 9. However, it is not limited to the one as described above. A single receiver element 90 may be constituted by a plurality of radio detectors.

Figure 11A:
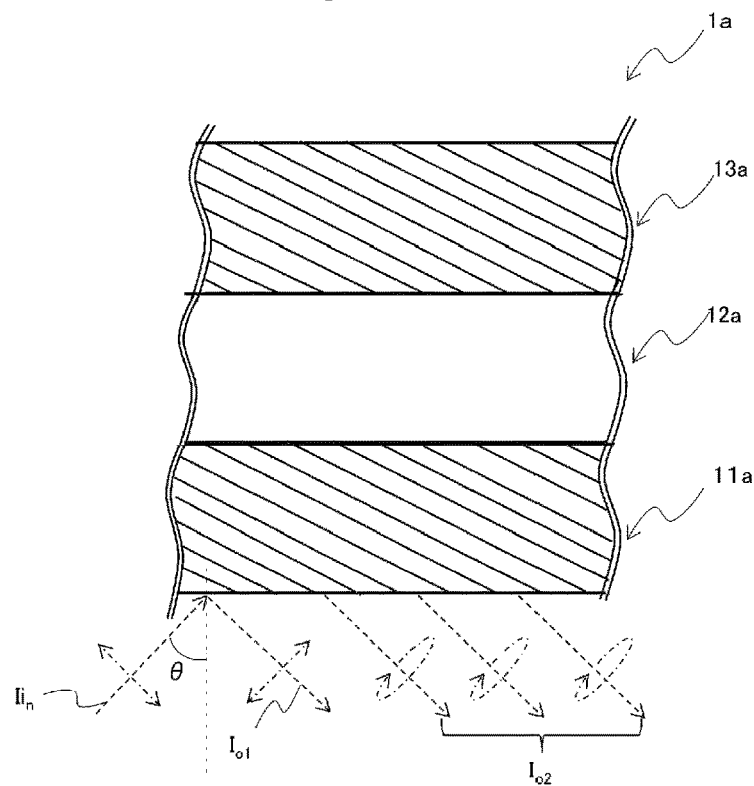
FIG. 11A is a schematic view showing the measurement subject having a multilayer membrane structure according to the second embodiment.
Figure 11B:
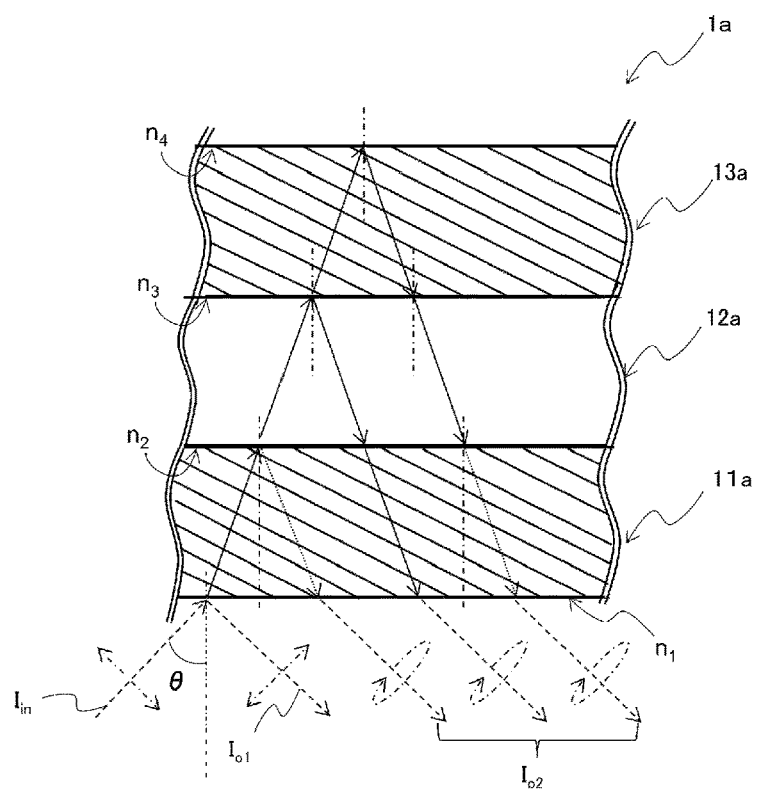
FIG. 11B is a schematic view showing a propagation process of the electromagnetic wave in the measurement subject having the multilayer membrane structure according to the second embodiment.

In the first and the second embodiments as shown in FIGS. 6 and 8, a case of the measurement subject 1 having a single layer was exemplified. The measurement device 100 is applicable to a multilayer laminated structure as shown in FIG. 11. As FIG. 11A shows, it is assumed that a measurement subject 1a as another example of the measurement subject 1 has three layers of a first layer 11a, a second layer 12a, and a third layer 13a. Referring to FIG. 11B, as each refractive index of the respective layers is different, the electromagnetic wave reflects on the boundary surface. That is, the intensity of the reflection electromagnetic wave received by the receiver 3 corresponds to a sum of intensities of the respective reflection electromagnetic waves reflecting on the boundary surfaces among the respective layers.

For example, the skin has a laminated structure. The skin is constituted by laminating such layers as a stratum corneum, an epidermis, a derma, and a subcutaneous tissue. The collagen that occupies 70% or more of the derma layer is a fibrous protein, and exhibits double refraction property.

If the water content of the stratum corneum is reduced to dry the environment (condition) of the inside of the skin, the electromagnetic wave is no longer absorbed in water. In such a state, the electromagnetic wave reaches further inside of the skin compared with the healthy skin. As a result, the receiver 3 may receive the electromagnetic wave that contains the polarization varied by the double refraction of the collagen that occupies 70% or more of the derma layer. That is, the polarization information may be monitored to allow monitoring of change in the skin condition.

Meanwhile, when the skin is dried to reduce the absorbed water content of the stratum corneum so that the electromagnetic wave reaches further inside of the skin deeper. Therefore, the thickness d of the measurement subject 1 is no longer regarded as being uniform. In this case, the polarization for monitoring water absorption in the stratum corneum is fixed to the specific polarization. Monitoring of the relative change in intensity of the polarization may clarify the change in the water content of the stratum corneum.

Third Embodiment

Figure 12:
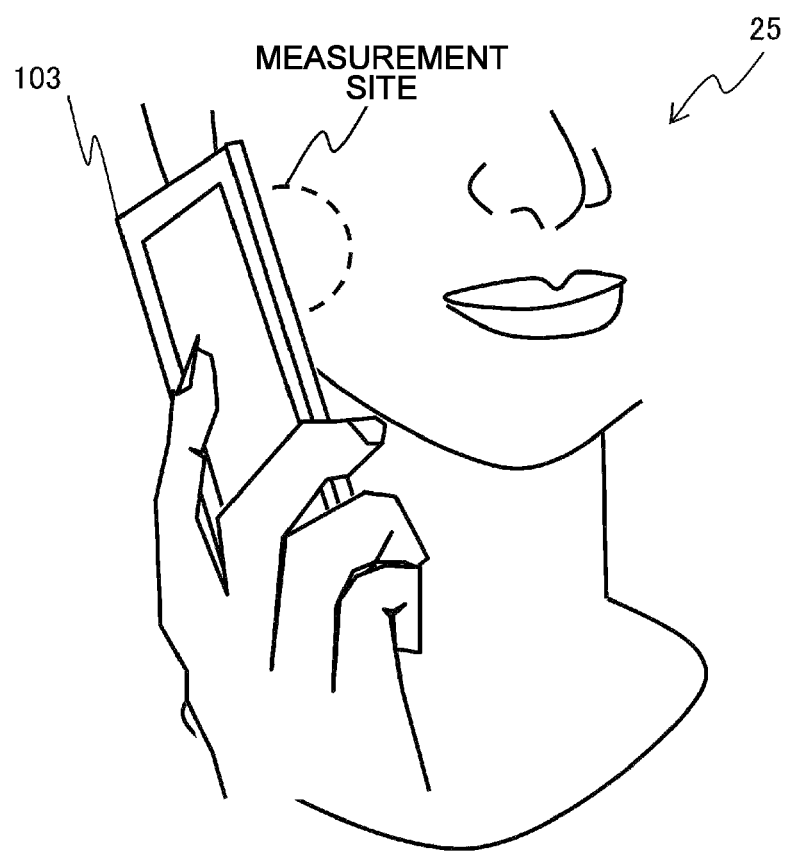
FIG. 12 is a schematic view showing a usage example of a skin information acquisition terminal according to a third embodiment.

An embodiment of an internal measurement result display system according to the present invention will be described. In this embodiment, a skin information acquisition terminal 103 as an example of the internal measurement result display system will be described. FIG. 12 shows a usage of the skin information acquisition terminal 103. The skin information acquisition terminal 103 is a portable information processor having a function that measures the internal condition of the skin (skin of the face in FIG. 12) of a user 25, and displays the measurement result. The skin information acquisition terminal 103 is operated in a predeteLmined contactless manner while being slightly separated from the side surface of the user 25 so that the internal condition of the skin of the user 25 (water content and the skin roughness degree) may be measured.

Figure 13A:
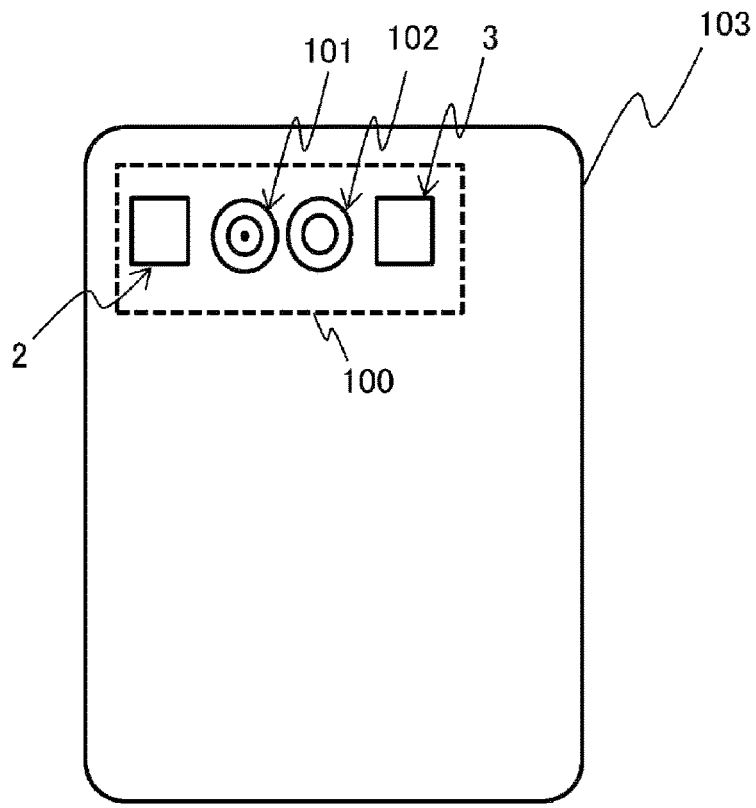
FIG. 13A is a schematic view showing a layout example of a radio transmitter, a receiver and an image pickup unit on the skin information acquisition terminal according to the third embodiment.
Figure 13B:
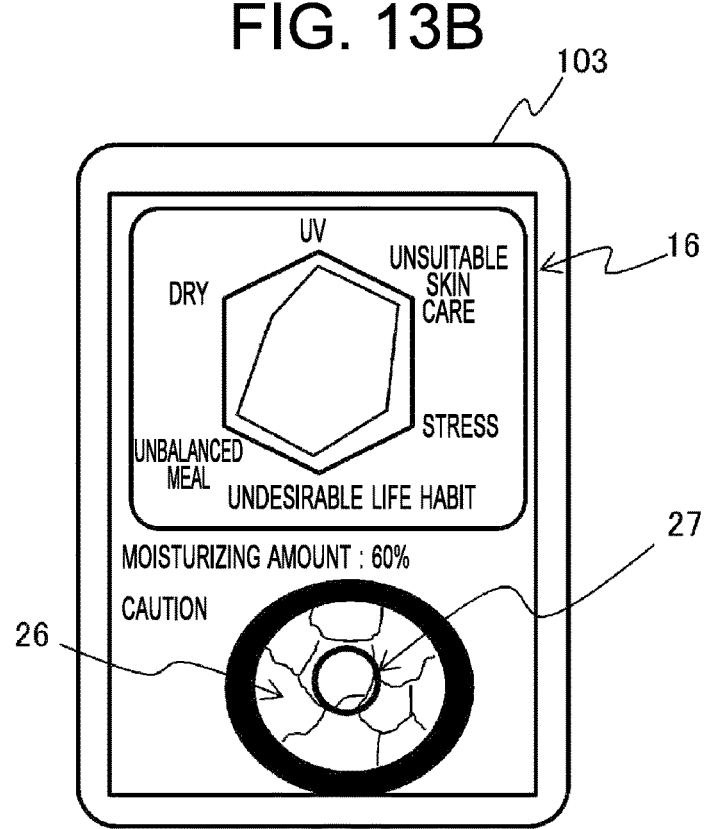
FIG. 13B is a schematic view showing a display unit of the skin information acquisition terminal according to the third embodiment.

FIG. 13A shows an appearance of the skin information acquisition terminal 103, showing a layout of a structure at the side facing the user 25 having the measurement subject 1. FIG. 13B shows a layout of the structure at the side on which the measurement result is displayed. The skin information acquisition terminal 103 of the embodiment is an example having the display side and the sensor side disposed on the different surfaces, respectively.

As FIG. 13A shows, the radio transmitter 2 and the receiver 3 of the measurement device 100 are disposed on the side facing the measurement subject. The radio transmitter 2 emits the electromagnetic wave to the measurement subject, and the receiver 3 receives the electromagnetic wave reflected by the measurement subject. As have been explained before, the radio transmitter 2 and the receiver 3 are disposed in the arrangement so that the incident angle θ of the electromagnetic wave emitted from the radio transmitter 2 to the measurement subject 1 becomes the value near the Brewster angle, and the reflection wave of the electromagnetic wave is received. A lens of an image pickup unit 101 as an incorporated camera, and a distance measurement unit 102 are disposed on the side facing the measurement subject.

As FIG. 13B shows, a display unit (display) 16 is disposed on the side opposite the surface facing the measurement subject, on which the result is displayed. Referring to FIG. 13B, the display unit 16 displays a photo 26 of the measurement subject overlapped with a measurement position marker 27 indicating the measurement position. The measurement position marker 27 displays that the measurement is conducted at the same site as the one for the last measurement.

Figure 14:
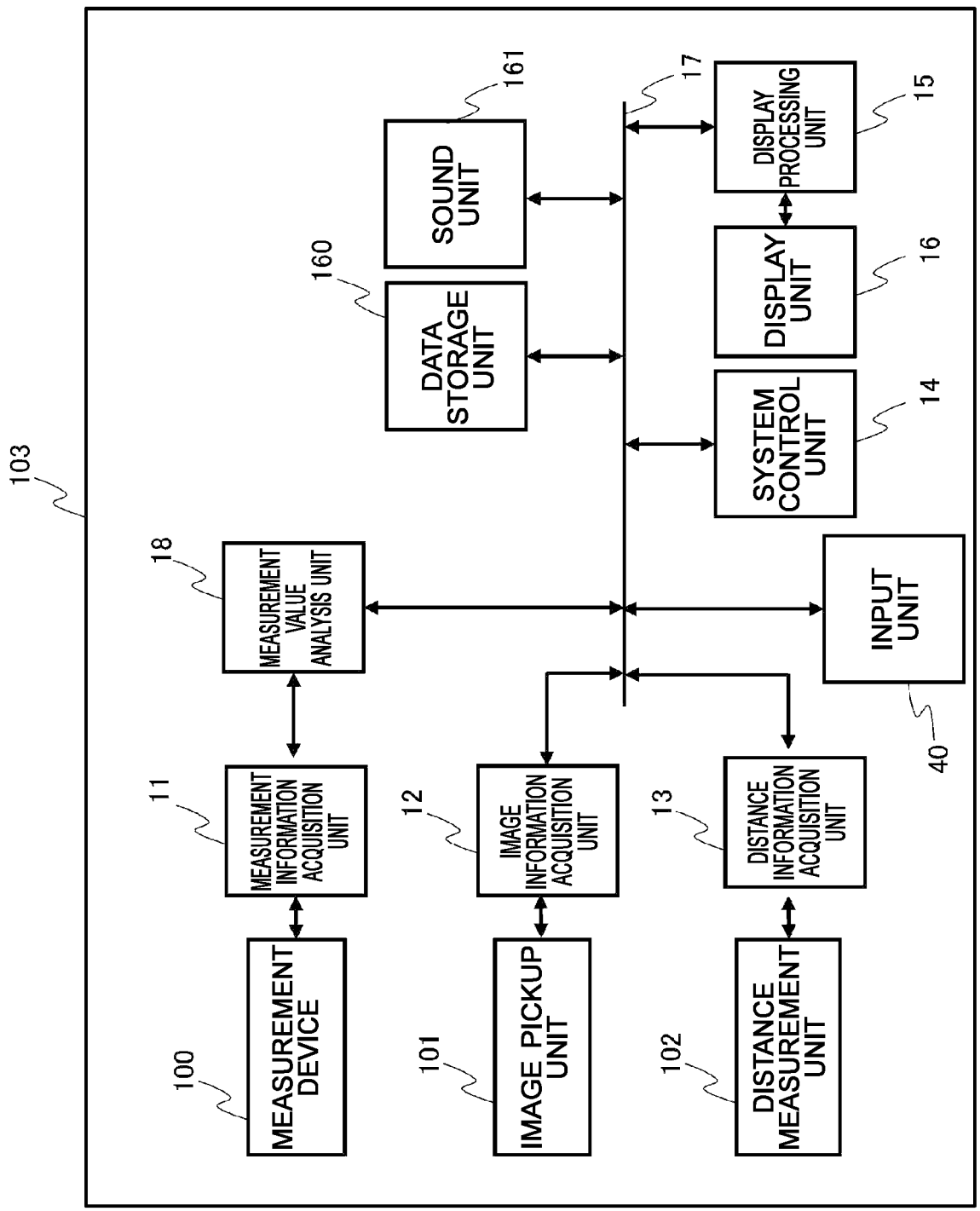
FIG. 14 is a schematic view showing an exemplary function structure of the skin information acquisition terminal according to the third embodiment.

FIG. 14 is a view showing a function structure of the skin information acquisition terminal 103 according to the embodiment. Referring to FIG. 14, operations of the skin information acquisition terminal 103 will be described.

The skin information acquisition terminal 103 picks up an image of a measurement site of the user 25 using the image pickup unit (camera) 101, and executes an image analyzing process for analyzing the photo. This makes it possible to display the analysis result such as ultraviolet light, dryness, stress, and the like on the display unit 16. The skin information acquisition terminal 103 acquires measurement values of water content inside the skin and skin texture (fineness) at the measurement site by the measurement device 100. The result of analyzing the measurement values is displayed on the display unit 16. For display here, as FIG. 13B shows, the photo 26 and judgement results (or notice of dryness, moisturizing amount, variation width) are displayed together.

It is possible to use an RGB camera with sensitivity to the visible light wavelength, a camera with sensitivity to infrared radiation, an RGB camera with sensitivity to the wavelength from infrared light to the visible light, and the like for the image pickup unit 101. It is possible to use an RGB camera with sensitivity to the wavelength from visible light to ultraviolet radiation, or from infrared light to the ultraviolet light via the visible light for the image pickup unit 101.

The distance measurement unit (distance sensor) 102 measures the distance between the measurement subject and the skin information acquisition terminal 103. The measured distance data is stored in a data storage unit 160. The distance measurement unit 102 allows estimation of the position of the skin information acquisition terminal 103 during the measurement for clarifying that the same position as the last one is measured. For example, analyzing the distance information acquired by the distance measurement unit 102, and the image acquired by the image pickup unit 101 allows estimation that the measurement subject is at the same position. When the skin information acquisition terminal 103 estimates that the same position is measured, a sound unit 161 to be described later may be used to generate a sound to notify the user 25.

FIG. 14 shows an example of a structure of the skin information acquisition terminal 103 according to the embodiment. Referring to FIG. 14, the respective units of the skin information acquisition terminal 103 will be described along with the conceptual process flow. Hereinafter, unless otherwise specified, it is assumed that the respective units constituting the skin information acquisition terminal 103 are controlled on the basis of signals from a system control unit 14 connected to those units via a system bus 17. As described above, the measurement device 100 is configured to adjust the arrangement of the radio transmitter 2 for emitting the electromagnetic wave, and the receiver 3 for receiving the electromagnetic wave reflected from the measurement subject 1 so that the incident angle θ to the measurement subject 1 becomes the value near the Brewster angle. In addition to the structure for adjusting the arrangement as described above, the measurement device 100 includes the main controller 4 that controls the radio transmitter 2 and the receiver 3, and the signal processor 5 that processes signals of the electromagnetic wave received by the receiver 3.

The information for identifying the user 25, and information relating to the measurement position (face, arm, and the like) is input via an input unit 40 (for example, touch sensor, button). Thereafter, a measurement information acquisition unit 11 acquires the signal processing results in the measurement device 100. As expressed by the formula 2, a measurement value analysis unit 18 calculates the ratio of the reflection intensity from the user 25 as the measurement subject 1. The measurement value analysis unit 18 refers to the past data accumulated in the data storage unit 160, and analyzes change in the skin condition of the user 25 as the time series data containing the past history in addition to the measurement value at the specific time. It is possible to store measurement data of a plurality of users in the data storage unit 160 by adding the numbers identifying the specific users. The measurement value analysis unit 18 executes the process for analyzing the polarization dependence characteristic based on the intensity and the polarization component of the received electromagnetic wave from the detection signal of the electromagnetic wave received by the receiver 3 of the measurement device 100.

The image pickup unit 101 then picks up an image of the measurement site of the user 25. An image information acquisition unit 12 acquires the picked up image. The distance measurement unit 102 measures the distance from the measurement site, and a distance information acquisition unit 13 acquires the result of the measured distance. Those measurement results are stored in the data storage unit 160. The display processing unit 15 executes the image analysis process from the picked up photo so that the display unit 16 displays such information as ultraviolet light, dryness, and stress. The display processing unit 15 allows the display unit 16 to display the results of analyzing the measurement values acquired from the measurement device 100 such as water content in the skin and skin condition (fineness) at the measurement site together with the photo 26. The content to be displayed on the display unit 16 may be the value such as the moisturizing amount, the graph of the variation width, and a radar view as exemplified in FIG. 13B.

In monitoring for a prolonged period of time, it is preferable to measure substantially the same measurement position through alignment. The system control unit 14 specifies the measurement position from the image results that have been picked up by the image pickup unit 101 last time or before, calculates measurement conditions from the result of distance measured by the distance measurement unit 102, and estimates the measurement position. It is possible to display the estimated measurement position on the display unit 16 like the measurement position marker 27 as shown in FIG. 13B. In this case, the system control unit 14 serves as a measurement position estimation unit. For example, when using the skin information acquisition terminal 103 configured as shown in FIG. 13A, it is impossible for the user 25 to confirm the display unit 16 of the skin information acquisition terminal 103 while picking up the image. In such a case, the sound unit 161 may be used to notify the information about the difference between the position indicated by the measurement position marker 27 acquired in the past and the position currently picked up by the image pickup unit 101 by a sound, for example, change in the tone, change in the volume, or the voice. In this case, the system control unit 14 serves as an arithmetic operation unit that executes the arithmetic operation to provide the difference between the position indicated by the past measurement position marker 27 and the currently picked up position. Based on the result arithmetically operated by the system control unit 14, the processing for obtaining the difference as described above is executed to determine the measurement position. The sound unit 161 includes an audio processor and a speaker. Referring to FIG. 14, each of the measurement information acquisition unit 11, the image information acquisition unit 12, the distance information acquisition unit 13, the measurement value analysis unit 18, the system control unit 14, an audio processor of the sound unit 161, and the display processing unit 15 is formed by the processor and the circuit for constituting the skin information acquisition terminal 103. The data storage unit 160 is formed by the memory constituting the skin information acquisition terminal 103.

Figure 15:
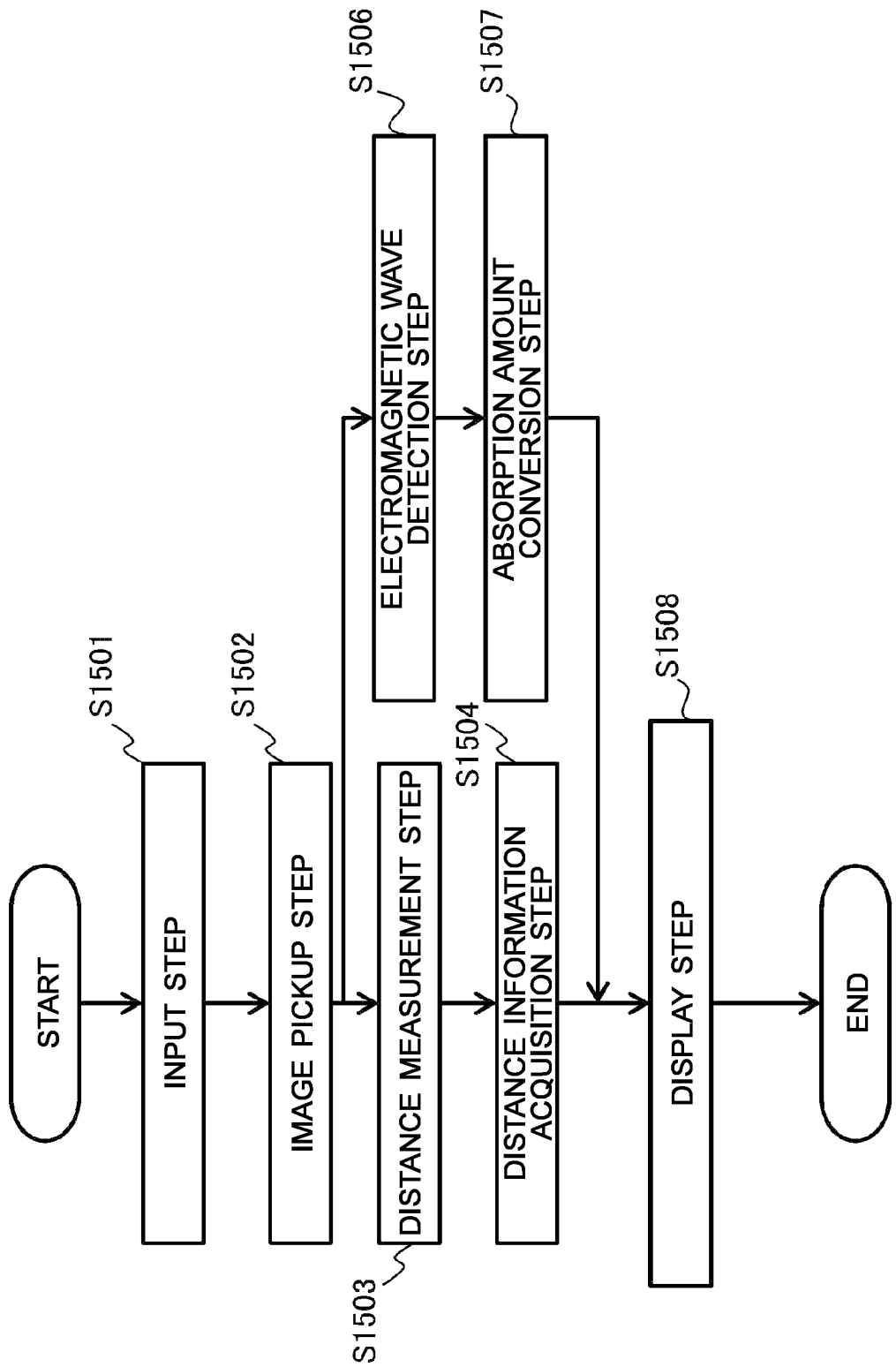
FIG. 15 is a flowchart representing an example of an operation for measuring the electromagnetic wave intensity and the polarization, performed by the skin information acquisition terminal according to the third embodiment.

The operation flow of the skin information acquisition terminal 103 will be described referring to the flowchart of FIG. 15. The system control unit 14 controls the input unit 40 to execute an input step in which an interface for inputting the information relating to the identification information and the measurement site is displayed for the user 25 (S1501). For example, in S1501, the input screen is displayed on the display unit 16 to allow the user 25 to input the prescribed information.

The system control unit 14 controls the image pickup unit 101 to execute an image pickup step that picks up an image of the measurement position of the user 25 (S1502).

The system control unit 14 then controls the distance measurement unit 102 to execute a distance measurement step that measures the distance between the measurement position of the user 25 and the skin information acquisition terminal 103 (S1503).

A distance information acquisition step is executed to allow the distance information acquisition unit 13 to acquire the measured distance result (S1504).

In order to calculate the position of the measurement position marker 27, a measurement position calculation step is executed for calculating the measurement position to the user 25 from results of positions of the radio transmitter 2 and the receiver 3 of the skin information acquisition terminal 103, and the distance obtained in S1504 (S1505). In S1505, it is judged whether or not the calculated measurement position coincides with the past measurement position to further execute an audio output step that outputs the sound corresponding to the judgement result using the sound unit 161. In this case, the judgement result in S1505 is synonymous with the estimation result of the measurement position. That is, the processing operation in S1505 is also executed as a measurement position estimation step.

The electromagnetic wave generator 7 of the radio transmitter 2 is controlled by the main controller 4 of the measurement device 100 through the system control unit 14 simultaneously with execution of a distance information acquisition step in S1504. Under the control as described above, an electromagnetic wave irradiation step that irradiates the electromagnetic wave with electromagnetic wave intensity $I_{in}$ to the user 25, and an electromagnetic wave detection step that acquires the intensity of the electromagnetic wave reflected by the user 25 are executed (S1506).

The measurement information acquisition unit 11 receives the electromagnetic wave intensity acquired in S1506 from the signal processor 5 so that the system control unit 14 executes an analysis step that analyzes the reflection electromagnetic wave intensity information and the polarization information from the received information. From the acquired information as expressed by the formula 2, the information on the absorption amount at the specific time and the polarization is added to execute an absorption amount conversion step for conversion into the absorption amount for each polarization (S1507). In an analysis stage of S1507, it is possible to conduct conversion into relative change in the water content in comparison with the water content as the past data stored in the data storage unit 160.

The measurement position and the analysis result of intensity/polarization signal derived from S1505 and S1507, respectively, and the image picked up in S1502 are processed by the display processing unit 15 so that a display step is executed for displaying the screen as shown in FIG. 13B on the display unit 16 (S1508).

The present invention is not limited to the embodiments as described above, but includes various modifications. For example, the embodiment is described in detail for readily understanding of the present invention which is not necessarily limited to the one equipped with all structures as described above. It is possible to replace a part of the structure of one embodiment with the structure of another embodiment. The one embodiment may be provided with an additional structure of another embodiment. It is further possible to add, remove, and replace another structure to, from and with a part of the structure of the respective embodiments.

For example, when using a monocular camera that allows pickup of the color image and the distance image simultaneously, separate functions, for example, the image pickup unit 101 and the distance measurement unit 102 may be implemented as a single function. This makes it possible to provide the compact and low-cost skin information acquisition terminal 103. The skin information acquisition terminal 103 is not limited to the terminal to be exclusively used for measuring the skin condition. For example, it is possible to employ a compact light source such as a resonant tunnel diode, and a compact detector such as a hetero barrier diode and a carbon nanotube for the radio transmitter 2 and the receiver 3 of the skin information acquisition terminal 103. This makes it possible to combine such terminal with the mobile phone (smartphone) with various information processing functions.

Figure 16:
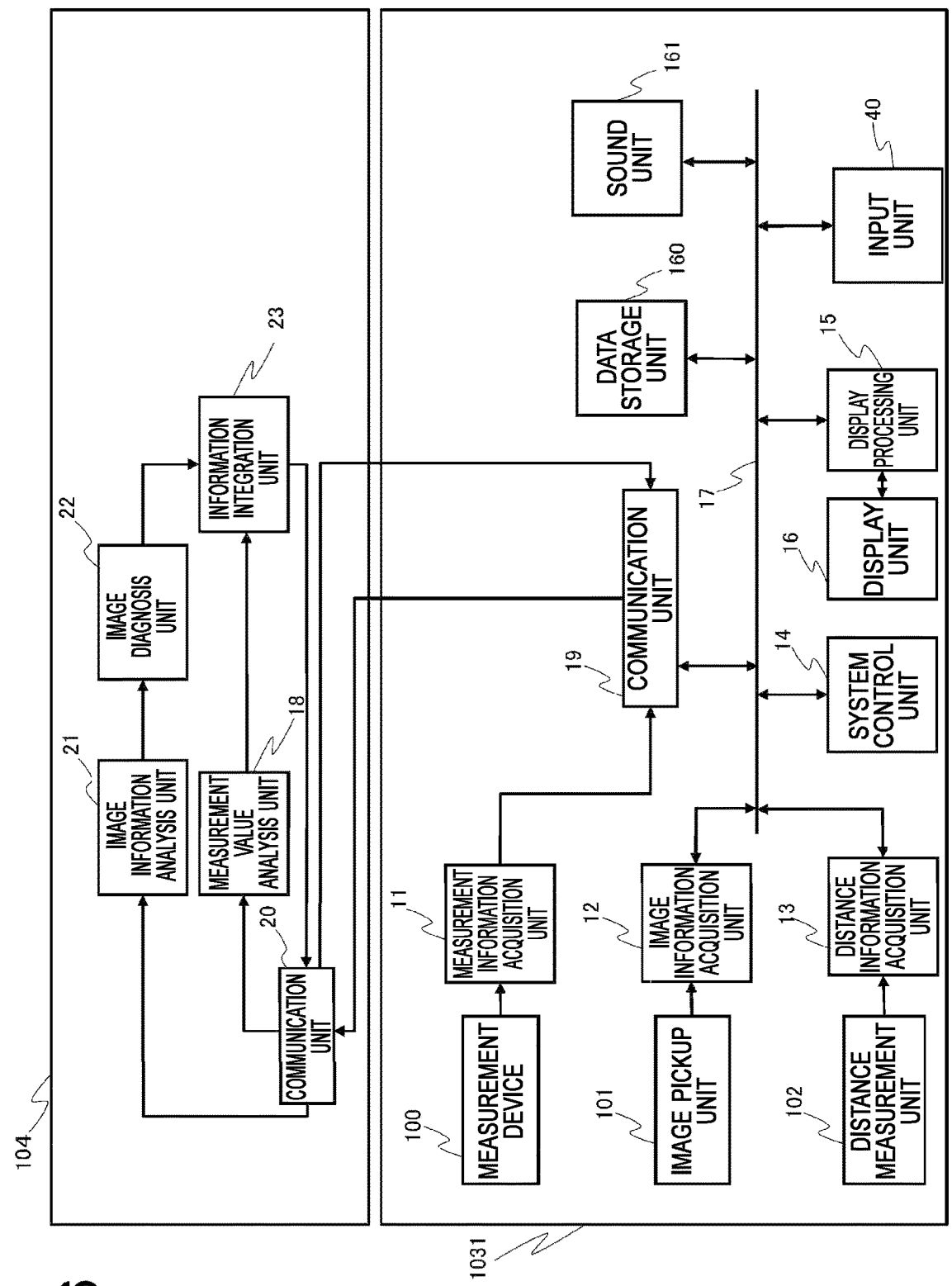
FIG. 16 is a schematic view showing another exemplary function structure of the skin information acquisition terminal according to the third embodiment.

FIG. 14 shows an example of the structure of the skin information acquisition terminal 103 according to the embodiment. However, all the analyzing process steps do not have to be executed by the skin information acquisition terminal 103. For example, the use of a skin information acquisition terminal 1031 with a communication unit 19 as shown in FIG. 16 allows an external server 104 to execute the complicated analyzing process entirely or partially. When using the external server, an information integration unit 23 of the server 104 is added for execution of the integration process in S1508 so that the processing load to the display processing unit 15 is reduced. The effect for improving the frame rate of the display unit 16 may be expected.

As FIG. 16 shows, the skin information acquisition terminal 1031 associated with the server 104 includes the communication unit 19 for data communication with the server 104, and does not include the measurement value analysis unit 18. The function corresponding to the measurement value analysis unit 18 is disposed in the server 104. The server 104 includes an image information analysis unit 21, an image diagnosis unit 22, the information integration unit 23, and a communication unit 20 in addition to the measurement value analysis unit 18. The measurement value analysis unit 18, the image information analysis unit 21, the image diagnosis unit 22, and the information integration unit 23 are formed by computers such as CPU and circuit constituting the server 104. The communication units 19, 20 are constituted by network communication systems including hardware, for example, Wifi (registered trademark), communication connector such as 8P8C modular connector.

The image information analysis unit 21 analyzes the image (image of the measurement subject 1) acquired by the image information acquisition unit 12, and outputs the analysis result.

The image diagnosis unit 22 diagnoses the image acquired from the image information acquisition unit 12 based on the output from the image information analysis unit 21.

The information integration unit 23 outputs information integrated for display on the display unit 16 using the diagnosis result derived from the image diagnosis unit 22 and the analysis result derived from the measurement value analysis unit 18.

Figure 17:
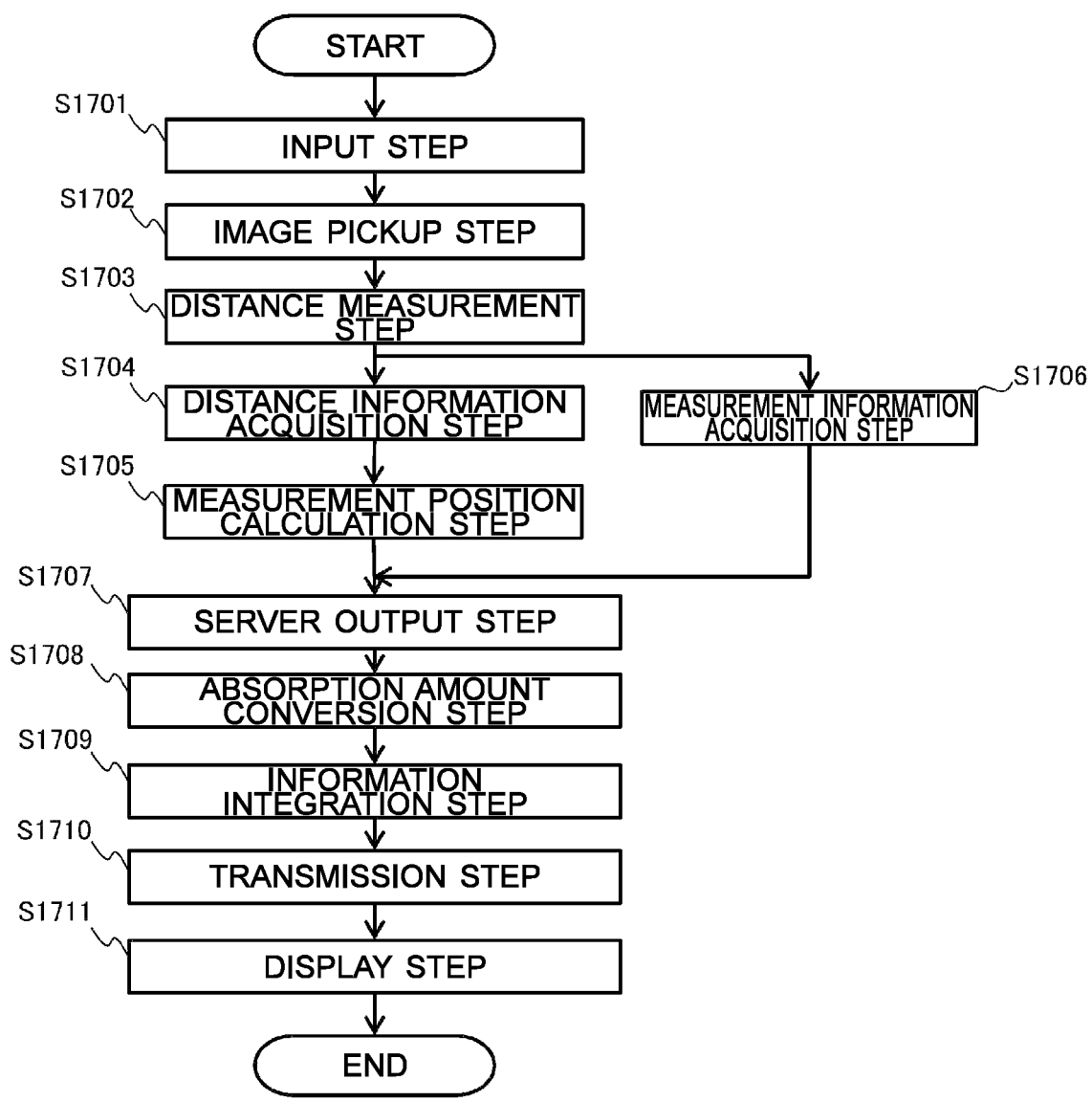
FIG. 17 is a flowchart representing another exemplary operation for measuring the electromagnetic wave intensity and the polarization using the skin information acquisition terminal according to the third embodiment.

The operation flow of the skin information acquisition terminal 1031 will be described referring to the flowchart of FIG. 17. The system control unit 14 controls the input unit 40 to execute an input step to provide the user 25 with the interface through which the identification information and the information relating to the measurement site is input (S1701). For example, an input screen is displayed on the display unit 16 in S1701 to allow the user 25 to input the prescribed information.

Then the system control unit 14 controls the image pickup unit 101 to execute an image pickup step that picks up an image of the measurement position of the user 25 (S1702).

The system control unit 14 controls the distance measurement unit 102 to execute a distance measurement step that measures the distance between the measurement position of the user 25 and the skin information acquisition terminal 1031 (S1703).

A distance information acquisition step is executed to allow the distance information acquisition unit 13 to acquire the measured distance result (S1704).

A measurement position calculation step is executed for calculating the measurement position of the user 25 from the positions of the radio transmitter 2 and the receiver 3 of the skin information acquisition terminal 1031, and the result of distance obtained in S1704 (S1705).

The electromagnetic generator 7 of the electromagnetic generation unit 2 is controlled by the main controller 4 through the system control unit 14 to irradiate the electromagnetic wave with emission electromagnetic wave intensity $I_{in}$ to the user 25 simultaneously with execution of the distance information acquisition step in S1704. A measurement information acquisition step is executed to acquire the reflection electromagnetic wave intensity information and the polarization information owing to reflection of the irradiated electromagnetic wave with emission electromagnetic wave intensity $I_{in}$ from the user 25 (S1706).

A server output step is executed for outputting the image picked up in S1702, the arithmetically operated result of the measurement position in S1705, and the reflection electromagnetic wave intensity information and the polarization information obtained in S1706 to the server 104 via the communication unit 19 (S1707). Thereafter, the absorption amount at the specific time is calculated from the acquired information as expressed by the formula 2 and the polarization information is added so that an absorption amount conversion step is executed for conversion into the absorption amount for each polarization (S1708). In S1707, upon output of data to the server 104 via the communication unit 19, the conversion into the relative change in the water content in the analysis stage in S1708 may be conducted referring to data stored in the data storage unit 160 partially or entirely.

An information integration step that integrates the information for display is executed so that the measurement position, the analysis result of the intensity/polarization signal, and the image picked up in S1702 are displayed by the server 104 as illustrated in FIG. 13B (S1709).

A transmission step is executed for transmitting the display information that has been integrated in S1709 from the server 104 to the communication unit 19 (S1710). Finally, a display step is executed for displaying the result of the integrated information processed in the display processing unit on the display unit 16 (S1711).

Figure 18A:
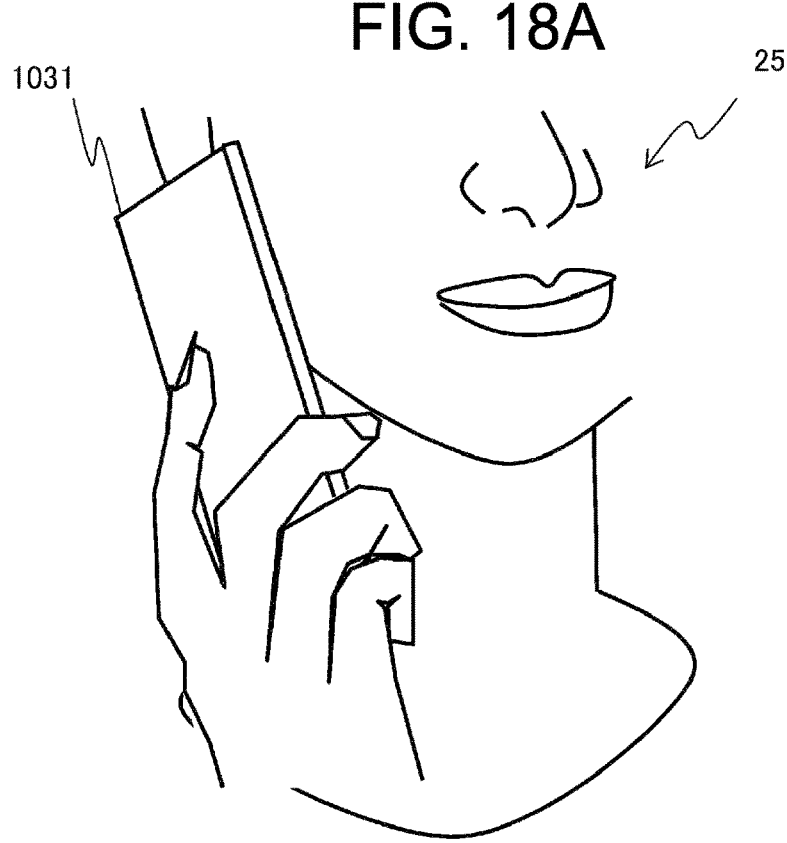
FIG. 18A is a schematic view showing another usage example of the skin information acquisition terminal according to the third embodiment.
Figure 18B:
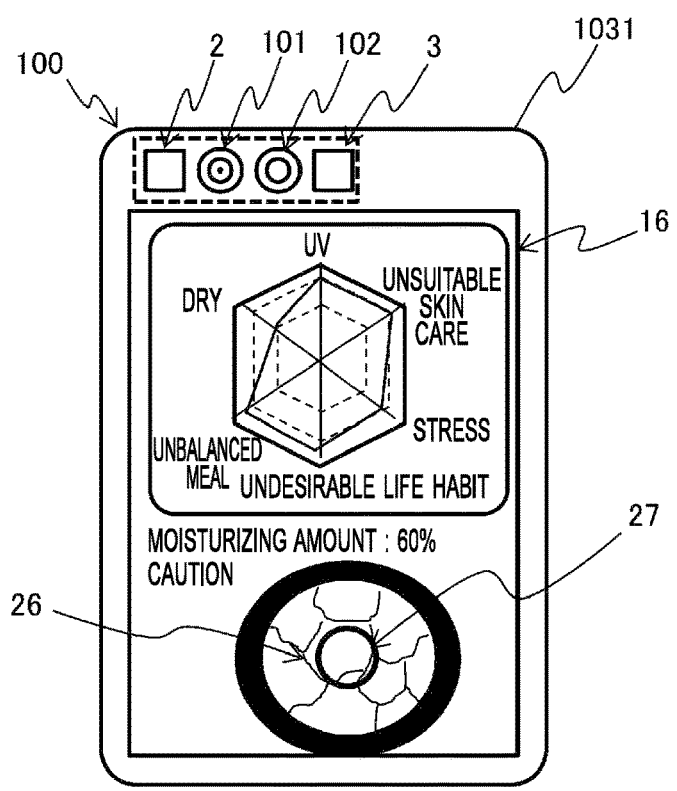
FIG. 18B is a schematic view showing another layout example of the radio transmitter, the receiver, and the image pickup unit on the skin information acquisition terminal according to the third embodiment.

The skin information acquisition terminal 103 as exemplified in FIG. 13 has the image pickup unit 101 and the display unit 16 disposed on opposite surfaces, respectively rather than on the same surface. With the above-structured terminal, the user 25 who is operating the image pickup unit 101 cannot perform such operation as alignment of the measurement position while viewing the display unit 16. As FIGS. 18A and 18B show, the image pickup unit 101 and the display unit 16 may be disposed on the same surface. The skin information acquisition terminal 103 structured as shown in FIGS. 18A and 18B allows the user 25 to adjust the measurement position while viewing the display unit 16, resulting in improved convenience.

The skin information acquisition terminal 103 may be configured to allow the user to confirm the display content on the display unit 16 while performing the image pickup operation, and allow the sound unit 161 to output sounds for notifying the difference between the measurement position marker 27 and the current position having its image picked up by the image pickup unit 101. In the case of deviation between the user's sense and the measurement value, the desired measurement width may be set by the user.

Fourth Embodiment

Figure 19:
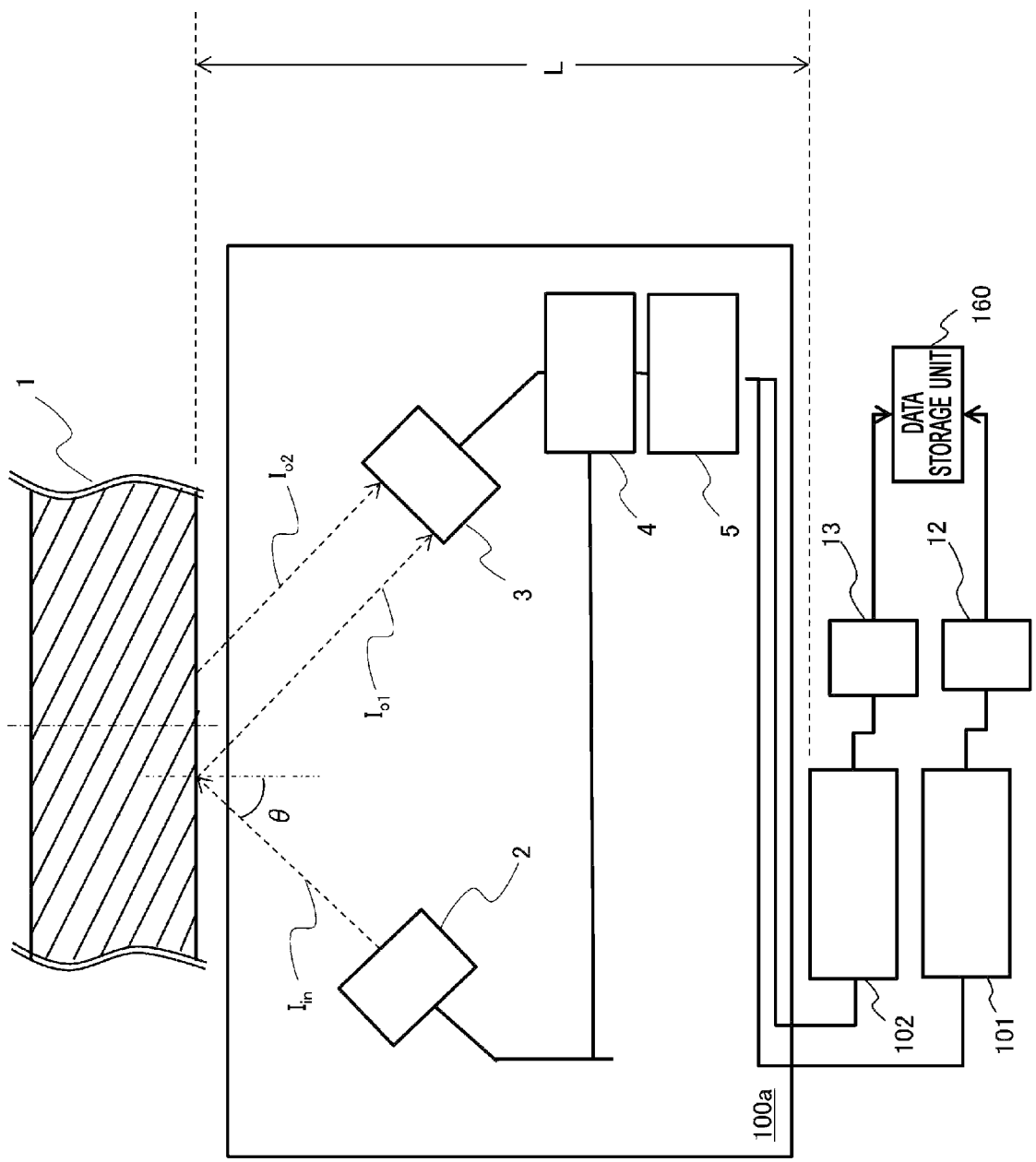
FIG. 19 is a schematic view of another exemplary structure of the contactless internal measurement device according to a fourth embodiment for observing the inside of the measurement subject.

Another embodiment of the contactless internal measurement device according to the present invention will be described. FIG. 19 is a view showing a structure of a measurement device 100a according to the embodiment. The measurement device 100a according to the embodiment has the similar structure to that of the measurement device 100 according to the first embodiment as described above, including the radio transmitter 2, the receiver 3, the main controller 4, and the signal processor 5. Characteristics of the structures and the arrangement condition are the same as those of the first embodiment, and detailed explanations thereof, thus will be omitted.

The measurement device 100a according to this embodiment further includes the image pickup unit 101, the image information acquisition unit 12, the distance measurement unit 102, the distance information acquisition unit 13, and the data storage unit 160. The structures are designated with the same codes as those of the structures of the skin information acquisition terminal 103 of the third embodiment, and have the same functions. When using the monocular camera capable of acquiring the color image and the distance image simultaneously for the image pickup unit 101, the image pickup unit 101 and the distance measurement unit 102 do not have to be installed as individual structures.

For example, a photo of the measurement site of the user 25 is picked up by the image pickup unit 101, and the picked up image is acquired by the image information acquisition unit 12 as described in the third embodiment. The distance measurement unit 102 measures the distance from the measurement site of the user 25. The distance information acquisition unit 13 acquires the result of the measured distance. In this embodiment, as shown in FIG. 19, it is assumed that a target distance between the measurement device 100a and the measurement subject 1 is set to "L".

Figure 20A:
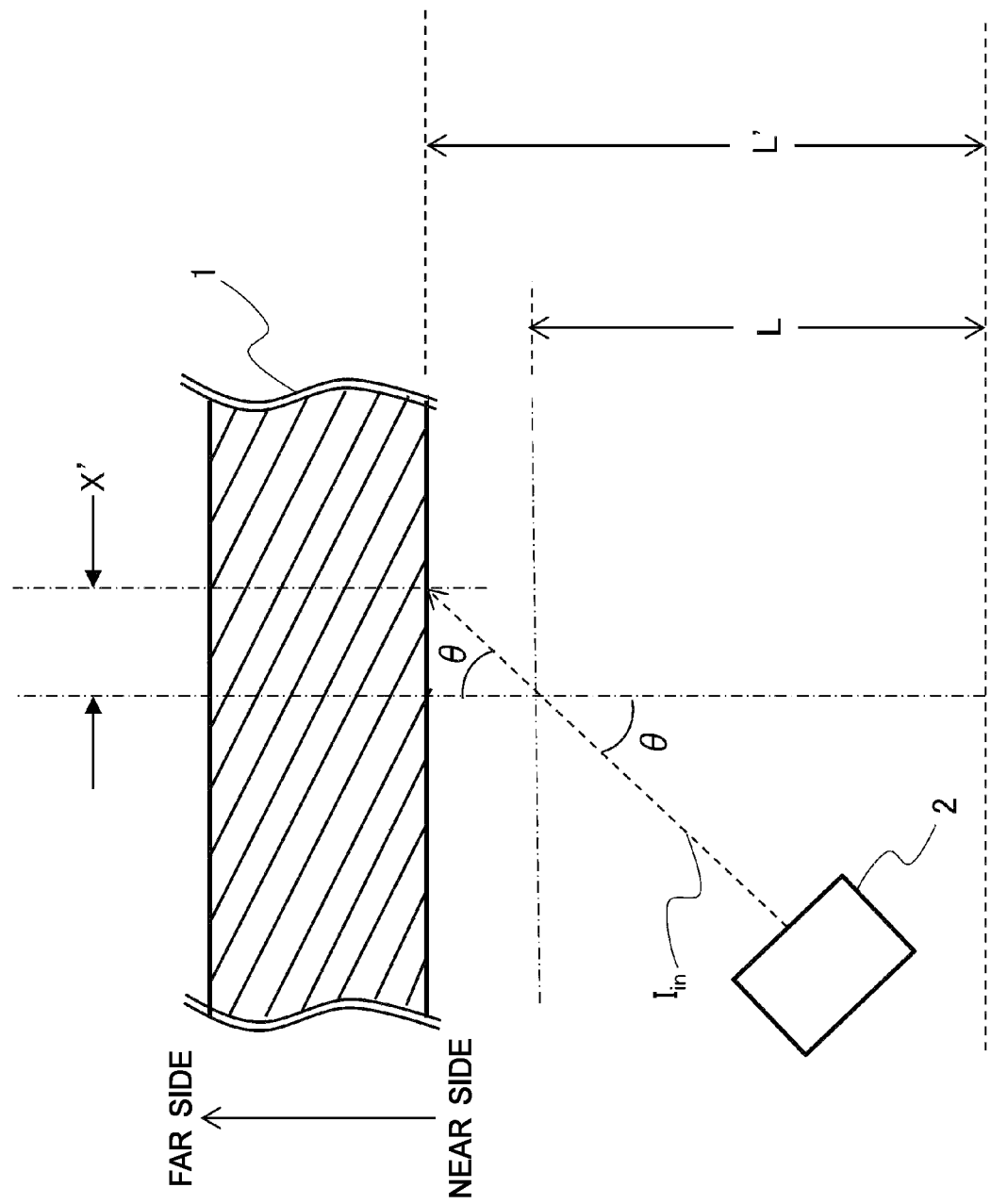
FIG. 20A is a schematic view of a measurement position which is displaced to a far side upon correction of the measurement position when measuring the electromagnetic wave intensity and the polarization using the skin information acquisition terminal according to the fourth embodiment.
Figure 20B:
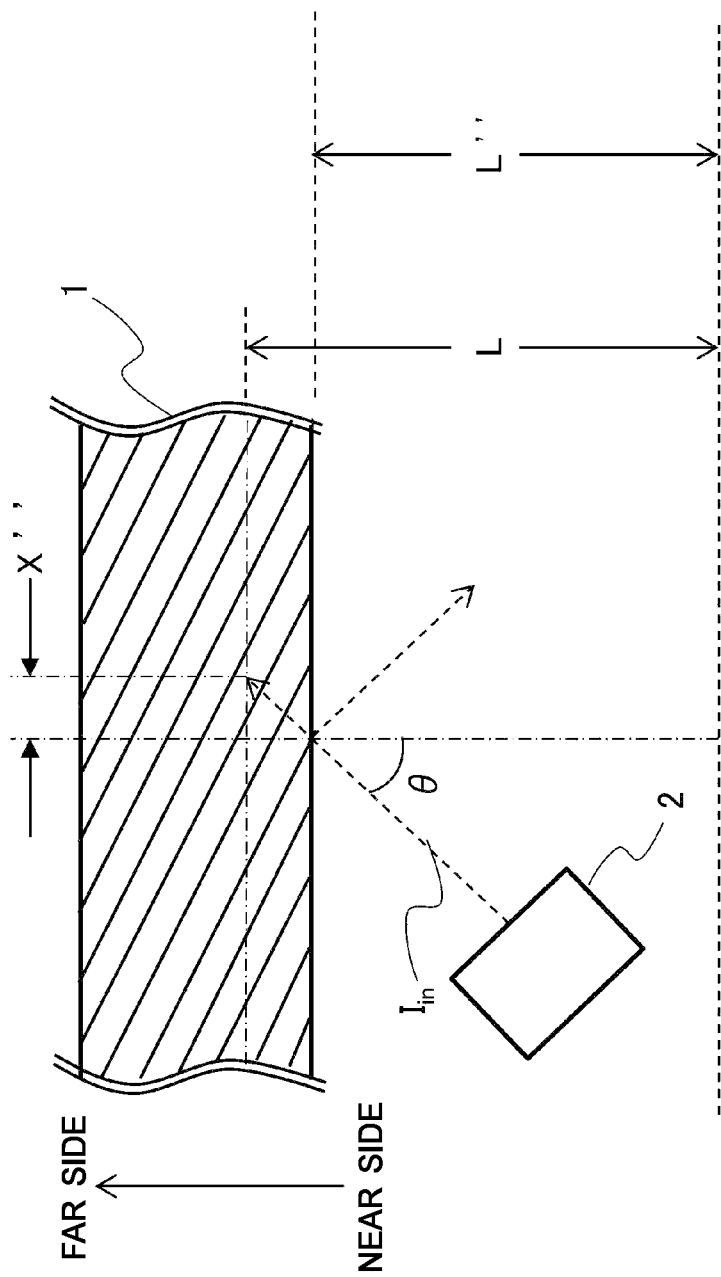
FIG. 20B is a schematic view of the measurement position which is displaced to a near side upon correction of the measurement position when measuring the electromagnetic wave intensity and the polarization using the skin information acquisition terminal according to the fourth embodiment.

FIG. 20 is an explanatory view of correcting the measurement position as a result of displacement in the distance between the surface of the measurement subject 1 (corresponding to the measurement site of the user 25) and the measurement device 100a. As FIG. 20A shows, if the measurement device 100a approaches the measurement subject 1 too close to the measurement subject 1 with respect to the target distance L, the electromagnetic wave irradiation position deviates from the target irradiation position of the measurement subject 1. This applies to the case where the measurement device 100a moves apart from the measurement subject 1 with respect to the target distance L as shown in FIG. 20B.

As FIGS. 20A and 20B show, a "far side" and a "near side" are defined on the assumption that the target distance L is set as an origin. The target distance L is defined as the distance between the measurement subject 1 and the measurement device 100a, which is set when the optical axis of the image pickup unit 101 coincides with the position where the electromagnetic wave emitted from the radio transmitter 2 is irradiated to the surface of the measurement subject 1 (corresponding to the measurement position of the user 25).

For example, FIG. 20A shows an exemplified case where the distance between the measurement device 100a and the measurement subject 1 becomes longer, and the measurement position displaces to the far side. FIG. 20B shows an exemplified case where the distance between the measurement device 100a and the measurement subject 1 becomes shorter, and the measurement position displaces to the near side.

In the case as shown in FIG. 20A, the position of the measurement position marker 27 may be derived from X'=|L−L'|tan θ. In the case as shown in FIG. 20B, the position of the measurement position marker 27 may be derived from X"=|L−L"|tan θ. The position of the measurement position marker 27 has to be corrected using the "X'" or "X"". The moving direction of the measurement device 100a may be determined in accordance with the codes of "X'" and "X"".

Figure 21:
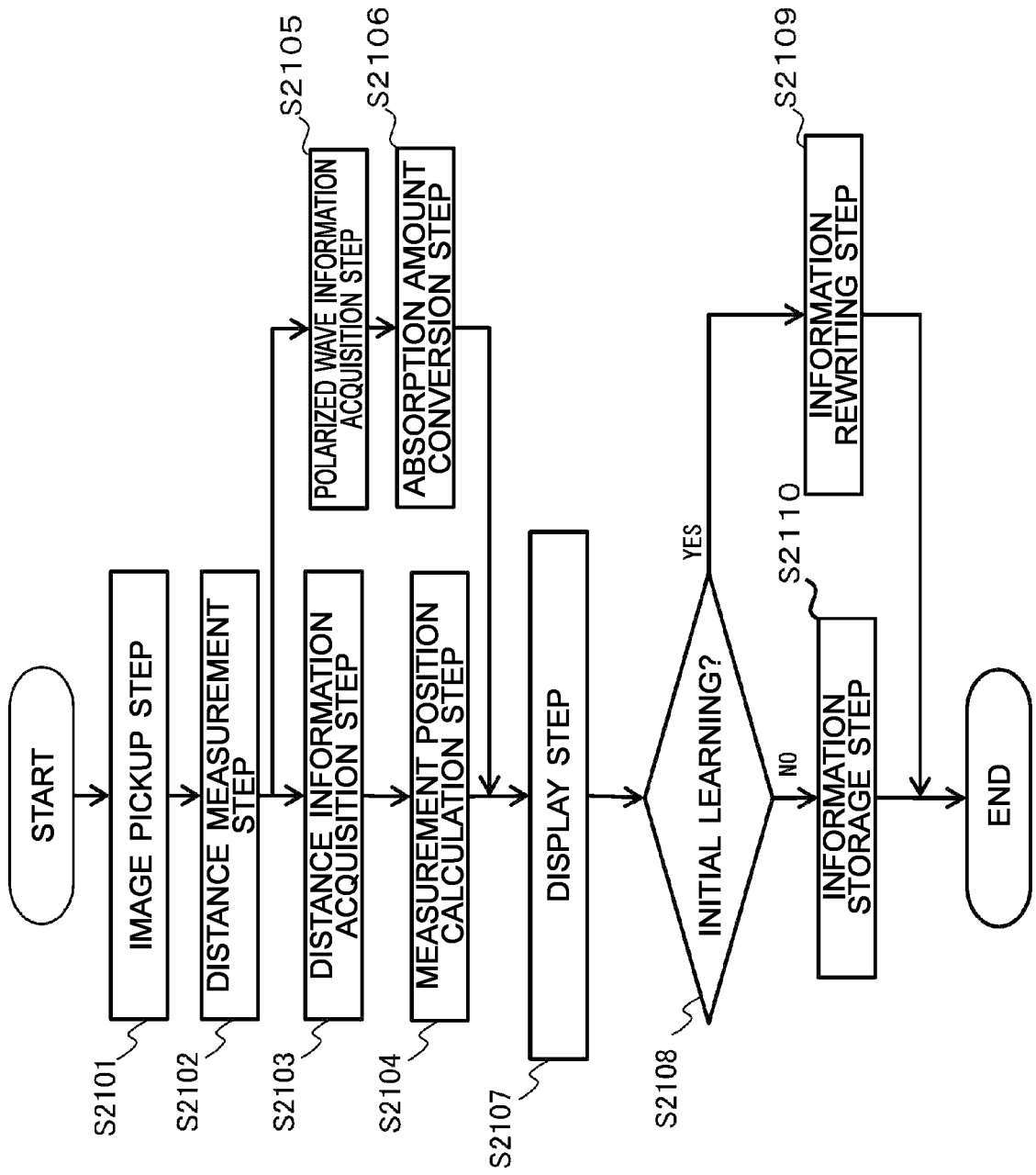
FIG. 21 is a flowchart representing an operation for measuring the electromagnetic wave intensity and the polarization using the skin information acquisition terminal according to the fourth embodiment.

The operation flow of the measurement device 100a will be described referring to the flowchart of FIG. 21. The main controller 4 controls the image pickup unit 101 to execute an image pickup step that picks up an image of the measurement position of the user 25 (S2101).

The main controller 4 controls the distance measurement unit 102 to execute a distance measurement step that measures the distance between the measurement subject 1 (corresponding to the measurement position of the user 25 in the third embodiment) and the measurement device 100a (S2102).

A distance information acquisition step is executed to allow the distance information acquisition unit 13 to acquire the result of measured distance (S2103).

As described referring to FIGS. 20A and 20B, the amount of the distance displaced either to the "near side" or the "far side" is calculated from the result derived from the positions of the radio transmitter 2 and the receiver 3 of the measurement device 100a, and the distance obtained in S2103. A measurement position calculation step is executed for calculating the measurement position from the amount of the displaced distance (S2104).

The electromagnetic wave generator 7 of the radio transmitter 2 is controlled by the main controller 4 simultaneously with acquisition of the distance information in S2103, and the electromagnetic wave with emission electromagnetic wave intensity $I_{in}$ is irradiated to the user 25. A step of acquiring electromagnetic wave intensity information and polarization information is executed for acquiring the electromagnetic wave intensity information and polarization information reflected from the user 25 (S2105).

The absorption amount at the specific time is calculated from the acquired information as expressed by the formula 2, and the polarization information is added to execute an absorption amount conversion step for conversion into the absorption amount for each polarization (S2106). It is possible to conduct the conversion into the relative change in the water content in comparison with the water content as the past data stored in the data storage unit 160 in S2106.

The display processing unit 15 processes the measurement position and the results of analyzing intensity/polarization signal obtained in S2104 and S2106 respectively, and the image picked up in S2101 to execute a display step that displays the screen as shown in FIG. 18B on the display unit 16 (S2107).

The main controller 4 executes an initial learning judgement step that judges whether or not the current measurement corresponds to the initial learning (S2108). S2108 is executed to acquire a reference value for observing the change in the condition (or time) of the measurement subject 1. The main controller 4 judges whether or not the past measurement value has been stored in the data storage unit 160. If the past measurement value is stored (S2108/YES), an information rewriting step is executed for rewriting the information that has already been stored in the data storage unit 160 by taking the picked up image, the measurement value, and the analysis results of intensity/polarization, which have been acquired in S2101 to S2107 as the reference values (S2109).

Meanwhile, in S2108, if the past measurement value is not stored (S2108/NO), a storage step is executed for storing a difference between the picked up image, the measurement value, and the analysis results of intensity/polarization acquired in S2101 to S2107, and the reference values stored in the data storage unit 160 (S2110). The measurement value, and the analysis results of intensity/polarization acquired in S2101 to S2107 may be stored as a new reference values in step S2110.

The present invention is not limited to the embodiments as described above, but includes various modifications. For example, the embodiment is described in detail for readily understanding of the present invention which is not necessarily limited to the one equipped with all structures as described above. It is further possible to replace a part of the structure of one embodiment with the structure of another embodiment. The one embodiment may also be provided with an additional structure of another embodiment. It is further possible to add, remove, and replace the other structure to, from and with a part of the structure of the respective embodiments.

The skin information acquisition terminal 103 is not limited to the terminal to be exclusively used for measuring the skin condition. For example, the use of a compact light source such as a resonant tunnel diode and a compact detector such as a hetero barrier diode and a carbon nanotube for the radio transmitter 2 and the receiver 3 makes it possible to combine the skin information acquisition terminal 103 with the smartphone. It is also possible to add such information as date and time, temperature and weather derived from the smartphone upon storage of the data in S2110.

Fifth Embodiment

Another embodiment of the internal measurement result display system according to the present invention will be described. An expiration analysis terminal 105 according to the embodiment is intended to measure expiration of a human as the measurement subject. The expiration analysis terminal has a function for analyzing the component contained in the expiration, and displaying the analysis result using electromagnetic waves in a contactless manner. It is known that the expiration of the patient suffering from specific disease contains gas that is different from the component contained in the expiration of a healthy person. For example, the expiration of a diabetes patient contains a large quantity of acetone. The expiration of a chronic bronchitis patient tends to contain more carbon monoxide. The concentration of the acetone or the carbon monoxide may be measured using the electromagnetic wave in the terahertz frequency band. The expiration analysis terminal 105 is used on the assumption that it is configured to emit the electromagnetic wave at the frequency suitable for the measurement subject as described above. The water content may also be measured using the expiration analysis terminal 105.

Figure 22:
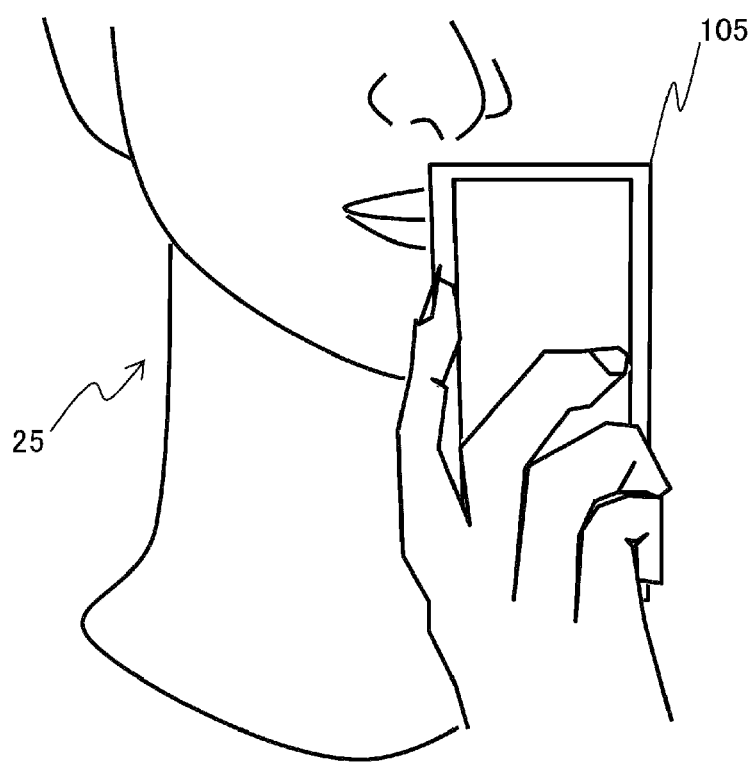
FIG. 22 is a schematic view showing a usage example of an expiration analysis terminal according to a fifth embodiment.

FIG. 22 shows the usage of the expiration analysis terminal 105. The expiration analysis terminal 105 includes an expiration measurement system 106 that analyzes the expiration of the user 25. As FIG. 22 shows, the expiration analysis terminal 105 is a portable information processing terminal having a function for analyzing the component contained in the expiration of the user 25 exhaling toward the expiration analysis terminal 105, and for displaying the analysis.

Figure 23A:
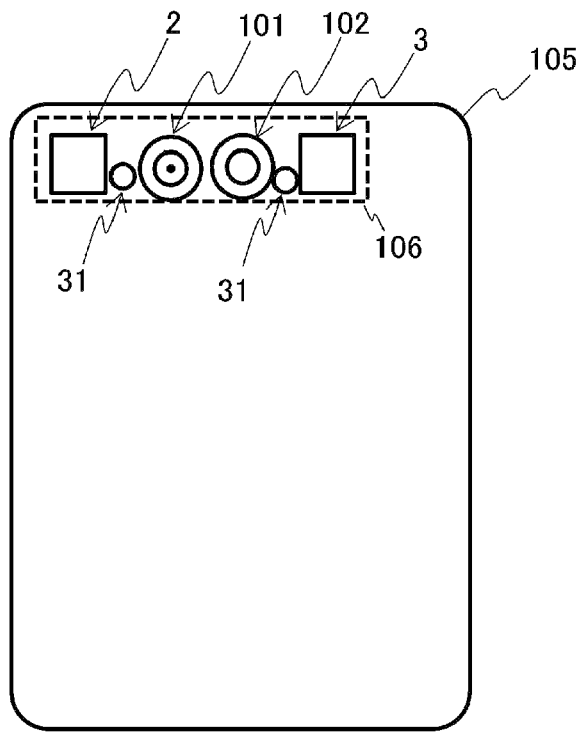
FIG. 23A is a schematic view showing a layout example of a radio transmitter, a receiver, and an image pickup unit on the expiration analysis terminal according to the fifth embodiment.
Figure 23B:
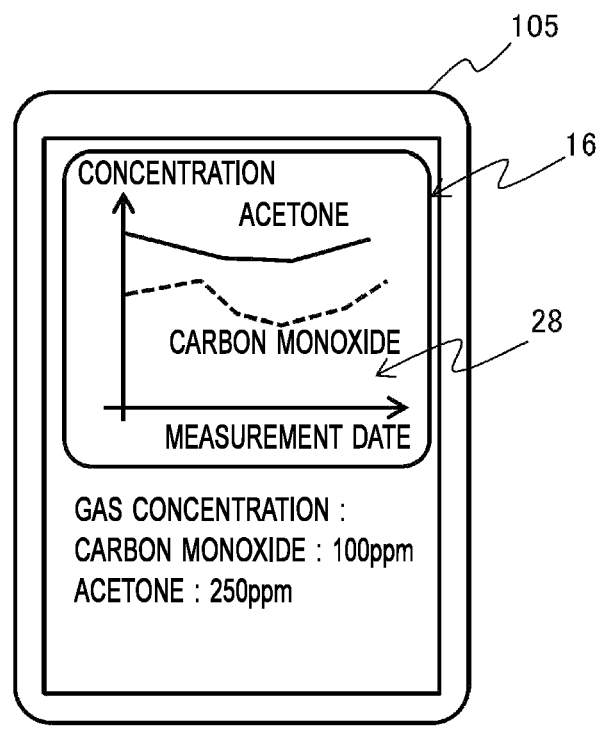
FIG. 23B is a schematic view showing a display unit disposed on the expiration analysis terminal according to the fifth embodiment.

FIGS. 23A and 23B are views each showing an appearance of the expiration analysis terminal 105. FIG. 23A schematically shows a side that receives the expiration of the user 25 to be analyzed. FIG. 23B shows the other side on which the expiration analysis result is displayed. As FIG. 23A shows, the expiration analysis terminal 105 has the side facing the user 25, on which the radio transmitter 2 and the receiver 3 of the expiration measurement system 106 are disposed. The radio transmitter 2 and the receiver 3 are disposed to interpose an opening of a gas passage 31. The lens of the image pickup unit 101 as an incorporated camera, and the distance measurement unit 102 are disposed on the same side.

As the image pickup unit 101 and the distance measurement unit 102 are similar to those described in the third embodiment, the detailed explanations thereof, thus will be omitted. It is possible to apply, for example, the RGB camera with sensitivity to the visible light wavelength, and the camera with sensitivity to the infrared light to the image pickup unit 101. It is also possible to apply the RGB camera with sensitivity to the wavelength from the infrared light to the visible light, from the visible light to the ultraviolet light, or from the infrared light to the ultraviolet light via the visible light. As described above, the image pickup operation allows automatic switching of the measurement mode between the skin and the expiration by confirming the image. The user 25 is allowed to switch the measurement mode by himself/herself.

As FIG. 23B shows, the expiration analysis terminal 105 allows the expiration measurement system 106 to measure the expiration component, and display the analysis result, for example, the concentration of carbon monoxide, acetone or the like on the display unit 16. It is possible to display the measurement value currently measured by the expiration measurement system 106 not only as the concentration, but also as a gas concentration measurement result 28 on the display unit. As shown in FIGS. 18A, 18B, in order to allow the user 25 of the expiration analysis terminal 105 to conduct the measurement while viewing the display (for example, concentration) on the display unit 16, the expiration measurement system 106, the image pickup unit 101, and the display unit 16 may be disposed on the same surface.

In order to give a notice on health to the user 25 who is confirming the display unit 16 of the expiration analysis terminal 105 while picking up the image, the user 25 may be notified of the current situation with sounds generated by the sound unit 161 in addition to the display of the notice and the relevant data. In the case of deviation between the user's sense and the measurement value, the user is allowed to set the desired value so that the user may be notified of the notice about the large deviation from the set value.

Figure 24:
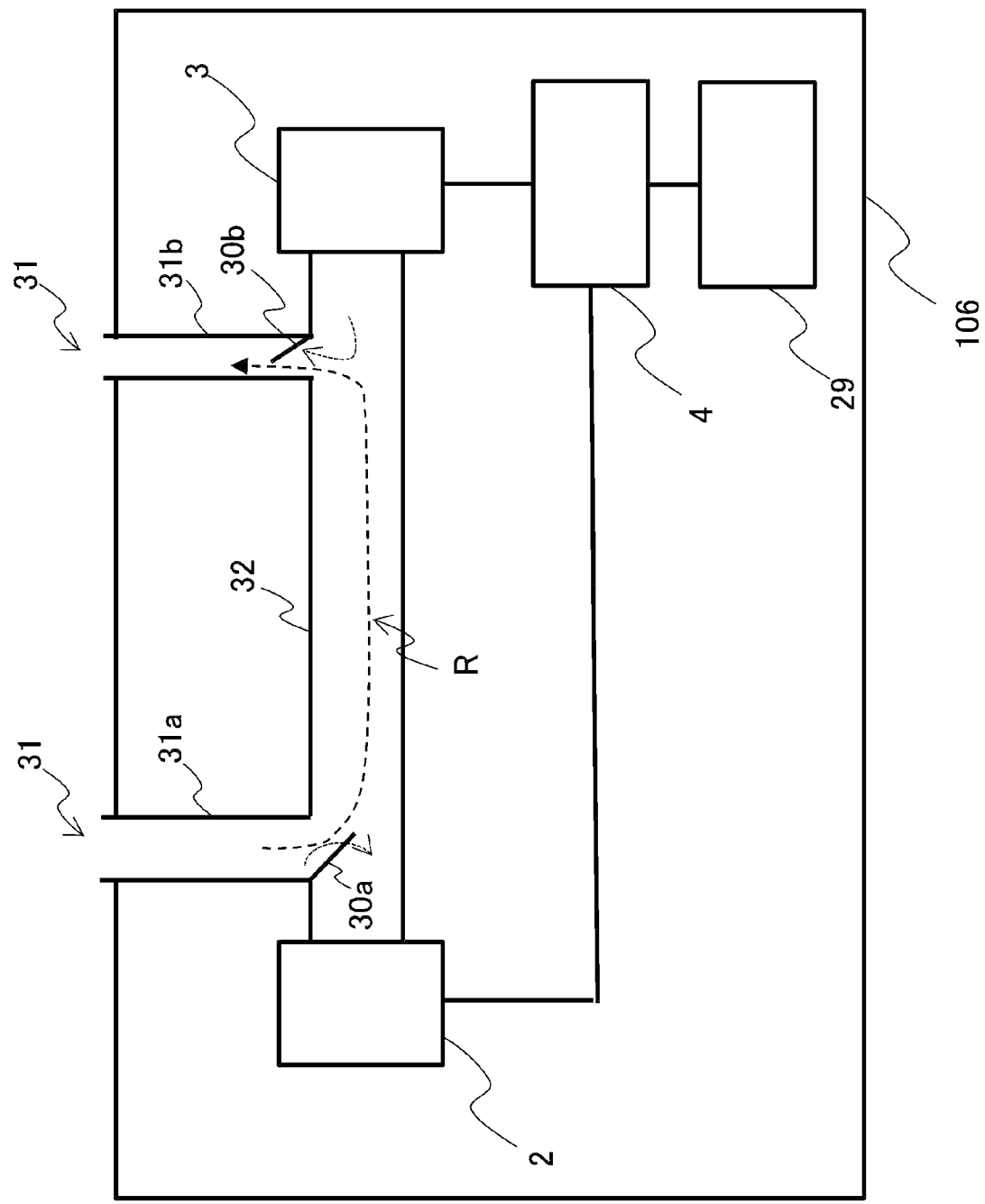
FIG. 24 is a schematic view showing an exemplary structure of the expiration measurement terminal according to the fifth embodiment.

FIG. 24 shows an exemplified structure of the expiration measurement system 106 according to this embodiment. As FIG. 24 shows, the expiration measurement system 106 includes the radio transmitter 2 that irradiates the electromagnetic wave suitable for the expiration as the measurement subject, the receiver 3 that receives the electromagnetic wave that has been changed under the influence of expiration, the main controller 4 that controls the radio transmitter 2 and the receiver 3, and a gas concentration measurement unit 29 that measures the prescribed gas concentration contained in the expiration based on the intensity of the electromagnetic wave received by the receiver 3.

The expiration measurement system 106 includes the gas passage 31 as the passage for the expiration, and a tubular gas concentration measurement space 32 which is communicated with the gas passage 31 and longitudinally extends between the radio transmitter 2 and the receiver 3. The gas passage 31 includes an expiration inflow passage 31a and an expiration exhaust passage 31b. The inflow passage 31a and the exhaust passage 31b are arranged as a pair around longitudinal ends of the gas concentration measurement space 32. Valves 30 which are opened and closed by an expiration flow R are disposed in openings of the inflow passage 31a and the exhaust passage 31b at the far side, respectively, that is, at the locations for communication between the inflow passage 31a and the gas concentration measurement space 32, and between the exhaust passage 31b and the gas concentration measuring space 32. An inflow valve 30a disposed in the inflow passage 31a is opened inward by inflow of the expiration. An exhaust valve 30b disposed in the exhaust passage 31b is opened outward while being pushed by the gas remaining inside upon inflow of the expiration to the gas passage 31.

The frequency of the electromagnetic wave emitted by the radio transmitter 2 to be used is readily absorbable by the gas component of the measurement subject. For example, if the expiration as the measurement subject is water vapor, it is preferable to set the electromagnetic wave at the frequency of 0.56 THz and 0.75 THz.

When the user 25 blows, the breathing force pushes the inflow valve 30a to be opened so that the expiration flows to the inside of the gas passage 31. If the electromagnetic wave is emitted from the radio transmitter 2 at this timing, the electromagnetic wave absorbed or attenuated by the component of the expiration is received by the receiver 3.

Figure 25:
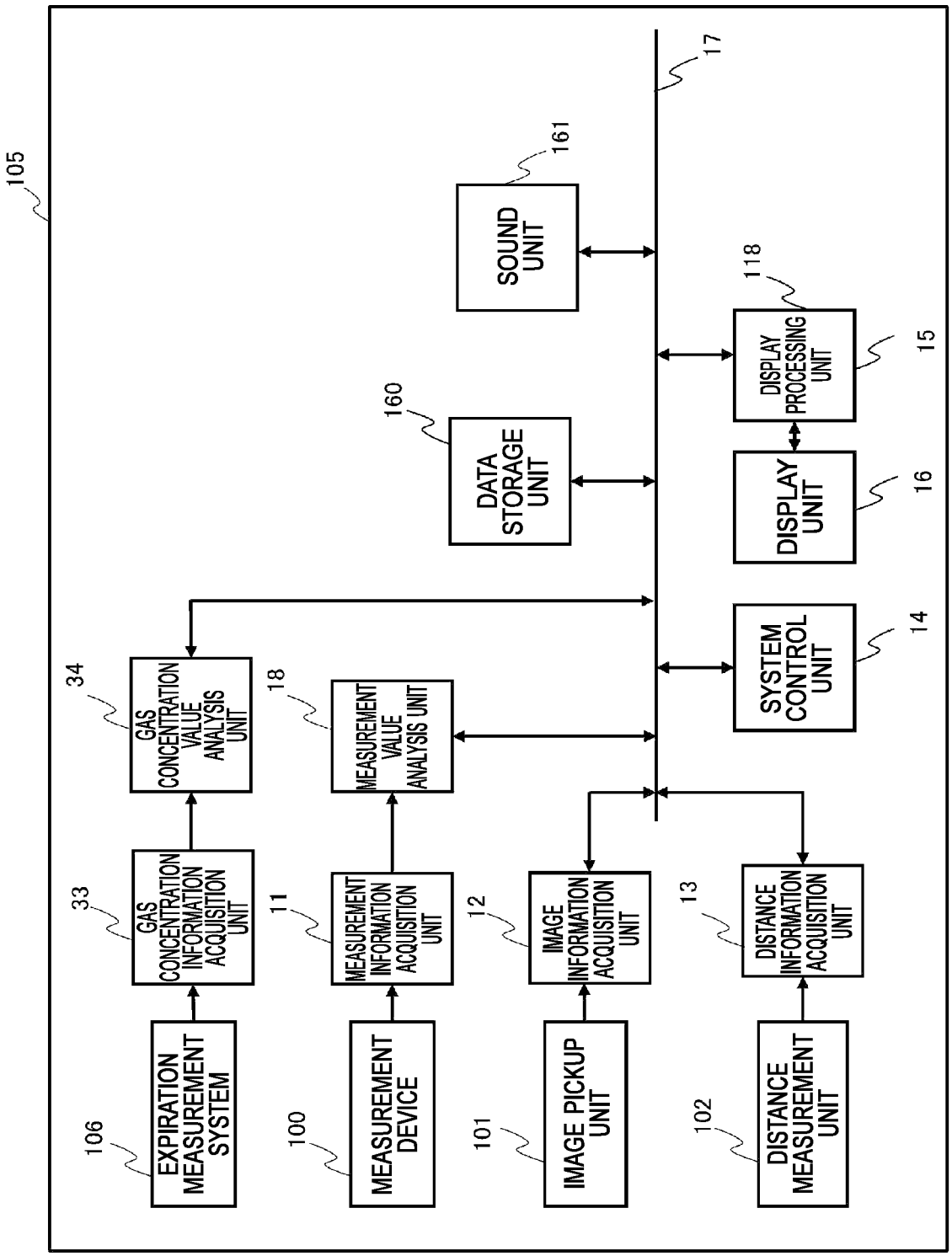
FIG. 25 is a schematic view showing an exemplary function structure of the expiration analysis terminal according to the fifth embodiment.

FIG. 25 shows an example of an exemplary structure of the expiration analysis terminal 105 according to the embodiment. The respective units of the expiration analysis terminal 105 will be described along with the conceptual process flow. Unless otherwise specified, the respective units constituting the expiration analysis terminal 105 are assumed to be controlled on the basis of signals from the system control unit 14 connected to those units via the system bus 17.

The expiration measurement system 106 includes the radio transmitter 2 that irradiates the electromagnetic wave to the expiration as the measurement subject, the receiver 3 that receives the electromagnetic wave that has been changed under the influence of expiration, the main controller 4 that controls the radio transmitter 2 and the receiver 3, and the gas concentration measurement unit 29 that measures the gas concentration of the electromagnetic wave received by the receiver 3. The radio transmitter 2 and the receiver 3 used for the expiration measurement system 106 may be common to those used in the measurement device 100 as described above. The radio transmitter 2 and the receiver 3 for the expiration measurement system 106 may be separately used from those used for the measurement device 100.

The gas concentration measured by the expiration measurement system 106 is acquired by a gas concentration information acquisition unit 33 and a gas concentration value analysis unit 34. The gas concentration information acquisition unit 33 acquires the gas concentration information as change in the electromagnetic wave under the influence of the expiration of the user 25 as the measurement subject 1 as expressed by the formula 2 from the intensity ratio between the irradiated electromagnetic wave and the reflection electromagnetic wave. The gas concentration value analysis unit 34 analyzes the gas concentration information, and acquires the gas concentration.

The gas concentration value analysis unit 34 is capable of analyzing change in the gas concentration of the expiration as time series data including not only the measurement value at specific time but also the past historical data by referring to the past data accumulated in the data storage unit 160. In this case, as shown in FIG. 23, the gas concentration measurement result 28 may be displayed on the display unit 16. In the expiration analysis terminal 105, the gas concentration information acquisition unit 33, the gas concentration value analysis unit 34, the measurement information acquisition unit 11, the image information acquisition unit 12, the distance information acquisition unit 13, the measurement value analysis unit 18, the system control unit 14, the sound processor of the sound unit 161, and the display processing unit 15 are constituted by the processors and circuits as components of the expiration analysis terminal 105. The data storage unit 160 is constituted by a memory as a component of the expiration analysis terminal 105.

The expiration measurement system 106 measures the ratio of the reflection intensity while changing the frequency of the electromagnetic wave in the prescribed range. This makes it possible to execute the process for specifying component of the gas from the peak frequency. Once the component of the gas is specified, the gas concentration may be measured.

Figure 26:
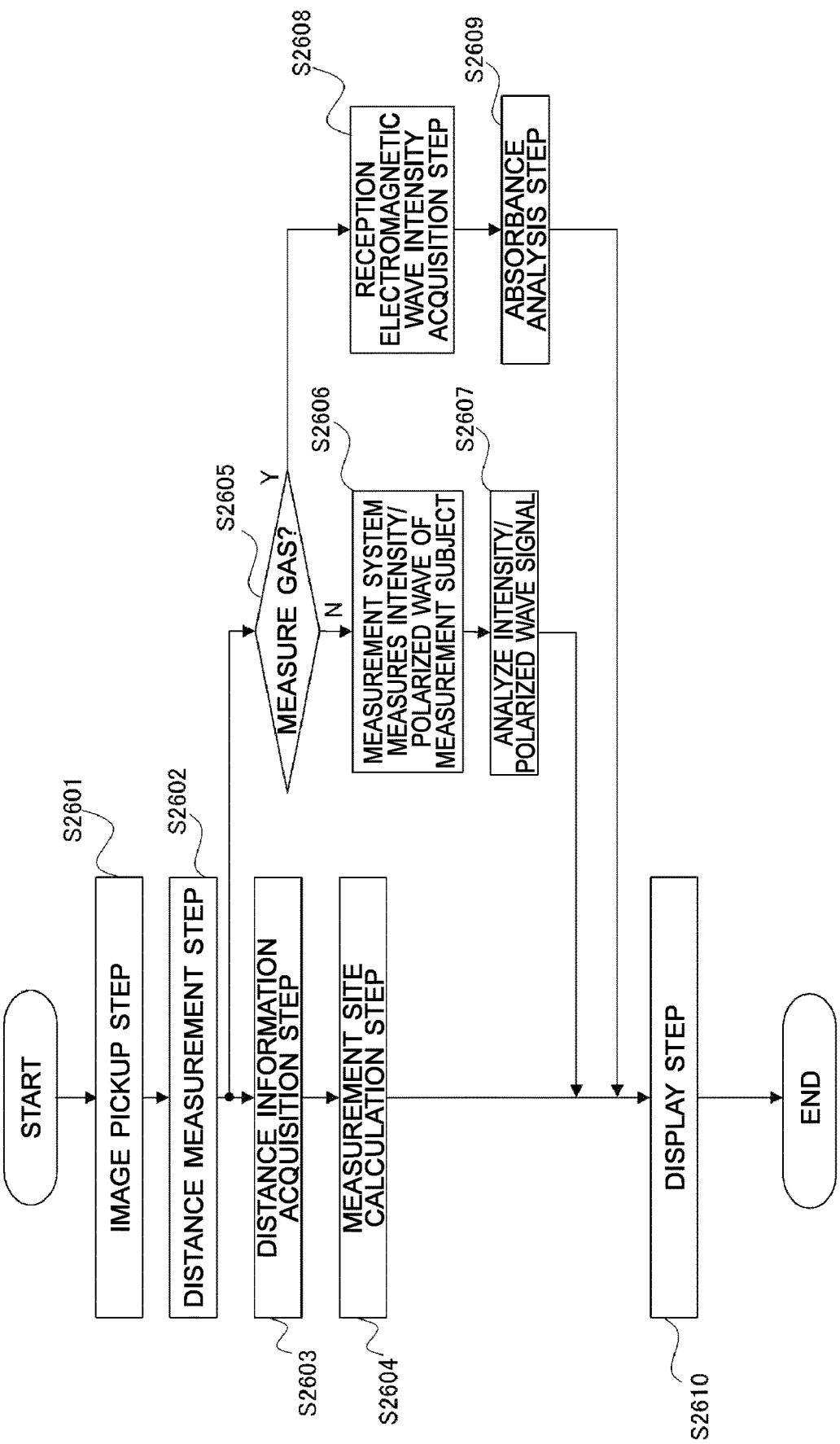
FIG. 26 is a flowchart representing an expiration measurement using the expiration analysis terminal according to the fifth embodiment.

The operation flow of the expiration analysis terminal 105 will be described referring to the flowchart of FIG. 26. The system control unit 14 controls the image pickup unit 101 to execute an image pickup step that picks up an image of the measurement position of the user 25 (S2601).

The system control unit 14 controls the distance measurement unit 102 to execute a distance measurement step that measures the distance between the measurement position of the user 25 and the expiration analysis terminal 105 (S2602).

A distance information acquisition step is executed to allow the distance information acquisition unit 13 to acquire the measured distance result (S2603).

A measurement position calculation step is executed for calculating the measurement position of the user 25 from the positions of the radio transmitter 2 and the receiver 3 of the expiration analysis terminal 105, and the result of the distance obtained in S2603 (S2604).

A measurement subject judgement step is executed for judging which of the gas concentration of the expiration and the skin is measured from the image picked up in S2601 simultaneously with execution of the distance information acquisition step in S2603 (S2605). In S2605, if it is judged that the measurement subject is the gas (S2605/Yes), the process proceeds to the flow for measuring the gas concentration. If it is judged that the measurement subject is not the gas in S2605 (S2605/No), the process proceeds to the flow for measuring the water content of the skin of the user 25.

In the flow for measuring the gas concentration, the main controller 4 controls the electromagnetic wave generator 7 of the radio transmitter 2 through the system control unit 14 to irradiate the emission electromagnetic wave intensity $I_{in}$ to the user 25. The main controller 4 controls the radio detector 9 of the receiver 3 to execute a reception electromagnetic wave intensity acquisition step that acquires the electromagnetic wave intensity of the electromagnetic wave that has passed the expiration of the user 25 (S2608).

An absorbance analysis step is executed for analyzing the absorbance to calculate the gas concentration at the specific time from the acquired information as expressed by the formula 2 (S2609).

The required measurement of the carbon monoxide of the user 25 will be described in detail. If the electromagnetic wave in the frequency band ranging from 10 GHz (0.1 THz) or higher to 30 THz or lower is irradiated to the carbon monoxide, the absorption spectrum appears in the steep state at equal intervals in the frequency band from approximately 0.4 THz to 2.5 THz. Accordingly, it is possible to use the electromagnetic wave at 1.5 THz to the expiration measurement system 106 as described above for measurement of the carbon monoxide. The use of the electromagnetic wave ranging from 0.4 THz to 0.6 THz allows measurement of the absorption spectra of the water vapor and the carbon monoxide in the narrow frequency range.

Compared with the past measurement value stored in the data storage unit 160, it may be converted into the change in the gas concentration in the analysis stage in S2609. The display processing unit 15 processes the measurement position and the analysis result of the absorbance obtained in S2604 and S2609 respectively, and the image picked up in S2601 to execute a display step that displays the screen as shown in FIG. 23B on the display unit 16 (S2610).

In the skin water content measurement flow, the main controller 4 controls the electromagnetic generator 7 of the radio transmitter 2 through the system control unit 14 to irradiate the emission electromagnetic wave intensity $I_{in}$ to the user 25. The main controller 4 controls the radio detector 9 of the receiver 3 to acquire the electromagnetic wave intensity information and polarization information reflected from the user 25 (S2606).

The absorption amount at the specific time is calculated from the information acquired as expressed by the formula 2, and the polarization information is added for conversion into the absorption amount for each polarization (S2607). In this case, the display processing unit 15 processes the measurement position and the analysis results of the intensity/polarization signal obtained in S2604 and S2607 respectively, and the image picked up in S2601 to display the screen as shown in FIG. 23B on the display unit 16 (S2610).

The present invention is not limited to the embodiments as described above, but includes various modifications. For example, the embodiments are described in detail for readily understanding of the present invention which are not necessarily limited to the ones equipped with all structures as described above. It is possible to replace a part of the structure of one embodiment with the structure of another embodiment. The one embodiment may be provided with an additional structure of another embodiment. It is further possible to add, remove, and replace another structure to, from and with a part of the structure of the respective embodiments.

REFERENCE SIGNS LIST

1 . . . measurement subject,
2 . . . radio transmitter,
3 . . . receiver,
4 . . . main controller,
5 . . . signal processor,
7 . . . electromagnetic wave generator,
8 . . . lens,
9 . . . radio detector,
10 . . . lens,
11 . . . measurement information acquisition unit,
12 . . . image information acquisition unit,
13 . . . distance information acquisition unit,
14 . . . system control unit,
15 . . . display processing unit,
16 . . . display unit,
17 . . . system bus,
18 . . . measurement value analysis unit,
19 . . . communication unit,
20 . . . communication unit,
21 . . . image information analysis unit,
22 . . . image diagnosis unit,
23 . . . information integration unit,
25 . . . user,
26 . . . photo,
27 . . . measurement position marker,
28 . . . gas concentration measurement result,
29 . . . gas concentration measurement unit,
30 . . . valve,
31 . . . gas passage,
32 . . . gas concentration measurement space,
33 . . . gas concentration information acquisition unit,
34 . . . gas concentration value analysis unit,
40 . . . input unit,
90 . . . receiver element,
91 . . . adder
91$a$ . . . adder,
91$b$ . . . adder,
91$c$ . . . adder,
91$d$ . . . adder,
100 . . . measurement device,
100$a$ . . . measurement device,
101 . . . image pickup unit,
102 . . . distance measurement unit,
103 . . . skin information acquisition terminal,
104 . . . server,
105 . . . expiration analysis terminal,
106 . . . expiration measurement system,
160 . . . data storage unit,
161 . . . sound unit,
1031 . . . skin information acquisition terminal

The invention claimed is:

1. A contactless internal measurement device comprising:
an electromagnetic wave irradiation unit that irradiates an electromagnetic wave to a measurement subject; and
an electromagnetic wave receiver that detects the electromagnetic wave reflected by the measurement subject,
wherein the electromagnetic wave irradiation unit is disposed to irradiate the measurement subject with the electromagnetic wave at an incident angle to reduce an intensity of a type of a polarization component of the electromagnetic wave detected by the electromagnetic wave receiver, the type of the polarization component being the same as a type of a polarization component of the electromagnetic wave irradiated by the electromagnetic wave irradiation unit.

2. The contactless internal measurement device according to claim 1, wherein the electromagnetic wave irradiation unit is disposed to allow the incident angle of the electromagnetic wave to the measurement subject to be near a Brewster angle.

3. The contactless internal measurement device according to claim 1,
wherein the electromagnetic wave receiver includes a plurality of electromagnetic wave detectors; and
each of the electromagnetic wave detectors has a size equal to or shorter than a wavelength of the electromagnetic wave irradiated by the electromagnetic wave irradiation unit.

4. The contactless internal measurement device according to claim 3, wherein the electromagnetic wave detector is disposed to detect an intensity of polarization component of an electromagnetic wave having a different type of a polarization component of the electromagnetic wave irradiated by the electromagnetic wave irradiation unit.

5. The contactless internal measurement device according to claim 3, wherein the electromagnetic wave detector is disposed to detect the polarization components in at least two directions or more, including a component in a polarization direction perpendicular to the same polarization direction as the polarization direction of the electromagnetic wave irradiated by the electromagnetic wave irradiation unit.

6. The contactless internal measurement device according to claim 1, wherein the electromagnetic wave irradiation unit further includes at least one lens; and the lens expands a region in which the electromagnetic wave irradiated from the electromagnetic wave irradiation unit to the measurement subject is regarded as a substantially parallel electromagnetic wave.

7. An internal measurement result display system comprising: the contactless internal measurement device according to claim 1;

an analysis unit that analyzes an intensity and a polarization dependence property from a signal received by the electromagnetic wave receiver;

a measurement unit that measures a distance from the measurement subject;

a measurement position estimation unit that estimates a measurement position from the distance obtained by the measurement unit; and a display unit that displays a picked up image of the measurement subject, wherein the display unit displays the measurement position estimated by the measurement position estimation unit from the distance obtained by the measurement unit together with an analysis result of the analysis unit.

8. The internal measurement result display system according to claim 7, further comprising an image pickup unit that picks up an image of the measurement subject.

9. The internal measurement result display system according to claim 7, further comprising:

a data storage unit that stores data relating to the distance measured by the measurement unit, and data relating to the measurement position estimated by the measurement position estimation unit; and an arithmetic operation unit that arithmetically operates a difference between the measurement position stored in the data storage unit and a measurement position having its image currently picked up, wherein based on a result of the arithmetic operation unit, the measurement position is determined.

10. The internal measurement result display system according to claim 7, further comprising:

a sound unit that notifies information relating to an estimation result of the measurement position by utilizing a sound; and an input unit that inputs the measurement position of the measurement subject, wherein the sound unit has a function of notifying information on a difference between the measurement position estimated by the measurement position estimation unit from the distance obtained by the measurement unit and the measurement position input through the input unit, by utilizing a sound.

11. A contactless internal measurement method comprising:

an electromagnetic wave irradiation step that irradiates an electromagnetic wave to a measurement subject; and an electromagnetic wave detection step that detects the electromagnetic wave reflected by the measurement subject, wherein in the electromagnetic wave irradiation step, the measurement subject is irradiated with the electromagnetic wave at an incident angle to reduce an intensity of a type of a polarization component of the electromagnetic wave detected in the electromagnetic wave detection step, the type of the polarization component being the same as a type of a polarization component of the electromagnetic wave irradiated to the measurement subject.

12. The contactless internal measurement method according to claim 11, wherein in the electromagnetic wave irradiation step, the electromagnetic wave is irradiated to allow the incident angle to the measurement subject to be near a Brewster angle.

13. The contactless internal measurement method according to claim 11, wherein the polarization components in at least two polarization directions or more are detected, including the polarization component in a direction perpendicular to the polarization direction of the electromagnetic wave irradiated to the measurement subject, and the polarization component different from the polarization component in the perpendicular direction among the polarization components of the electromagnetic waves detected in the electromagnetic wave detection step.

14. The contactless internal measurement method according to claim 11, further comprising:

an analysis step that analyzes an intensity and a polarization dependence property from a received signal;

a measurement step that measures a distance from the measurement subject;

a measurement position estimation step that estimates a measurement position from the distance from the measurement subject; and a display step that displays the estimated measurement position together with a result obtained in the analysis step.

15. The contactless internal measurement method according to claim 14, further comprising an image pickup step that picks up an image of the measurement subject, wherein in the display step, the estimated measurement position is displayed together with a result obtained in the analysis step, and a picked up image of the measurement subject.

16. The contactless internal measurement method according to claim 14, further comprising:

a sound output step that notifies information on an estimated result obtained in the measurement position estimation step by utilizing a sound; and an input step that inputs the measurement position of the measurement subject, wherein the sound output step outputs a sound indicating a difference between the estimated measurement position and the input measurement position.

* * * * *